US008330596B2

(12) United States Patent
Tanaka et al.

(10) Patent No.: US 8,330,596 B2
(45) Date of Patent: Dec. 11, 2012

(54) SENSOR NODE AND SENSOR NETWORK SYSTEM

(75) Inventors: Takeshi Tanaka, Akishima (JP); Shunzo Yamashita, Musashino (JP); Kiyoshi Aiki, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 514 days.

(21) Appl. No.: 12/155,457

(22) Filed: Jun. 4, 2008

(65) Prior Publication Data

US 2008/0309481 A1 Dec. 18, 2008

(30) Foreign Application Priority Data

Jun. 15, 2007 (JP) ................................ 2007-158474

(51) Int. Cl.
*G08B 1/08* (2006.01)

(52) U.S. Cl. ................ 340/539.12; 340/540; 340/573.1; 604/300; 604/503

(58) Field of Classification Search .............. 340/539.12
See application file for complete search history.

(56) References Cited

U.S. PATENT DOCUMENTS

| | | | | |
|---|---|---|---|---|
| 6,198,394 | B1 * | 3/2001 | Jacobsen et al. | 340/573.1 |
| 7,561,744 | B2 | 7/2009 | Hagiwara et al. | |
| 2004/0162466 | A1 * | 8/2004 | Quy | 600/300 |
| 2005/0114170 | A1 | 5/2005 | Park et al. | |
| 2006/0229520 | A1 | 10/2006 | Yamashita et al. | |
| 2006/0238333 | A1 * | 10/2006 | Welch et al. | 340/539.12 |
| 2007/0073266 | A1 * | 3/2007 | Chmiel et al. | 604/503 |
| 2007/0159321 | A1 | 7/2007 | Ogata et al. | |
| 2008/0018502 | A1 * | 1/2008 | Wegener | 341/50 |
| 2008/0177436 | A1 * | 7/2008 | Fortson | 701/29 |

FOREIGN PATENT DOCUMENTS

| | | |
|---|---|---|
| JP | 04-138129 | 5/1992 |
| JP | 06-205752 | 7/1994 |
| JP | 2001-061794 | 3/2001 |
| JP | 2005-514138 | 1/2003 |
| JP | 2006-520657 | 3/2004 |
| JP | 2004-141352 A | 5/2004 |
| JP | 2005-352881 | 6/2004 |
| JP | 2006-312010 | 8/2005 |
| JP | 2005-323326 A | 11/2005 |
| JP | 2007-184754 | 1/2006 |
| JP | 2006-304251 | 11/2006 |
| JP | 2007-007243 | 1/2007 |
| WO | WO 2004/084720 A2 | 3/2004 |

OTHER PUBLICATIONS

"ECG Data Compression Techniques—A Unified Approach", Jalaleddine et al., IEEE Transactions on Biomedical Engineering, vol. 37, No. 4, Apr. 1990.* "Wireless Sensor Network MOTE-2007 Q3", Crossbow, Ltd., 4 pages in Japanese, 1 page of translation in English.

* cited by examiner

*Primary Examiner* — Daniel Wu
*Assistant Examiner* — Frederick Ott
(74) *Attorney, Agent, or Firm* — Stites & Harbison, PLLC; Juan Carlos A. Marquez, Esq

(57) ABSTRACT

Provided is a sensor node including: a sensor for measuring biological information; a CPU for acquiring data by driving the sensor; a wireless communication unit for transmitting the data acquired by the CPU; a battery for supplying the control unit, the wireless communication unit, and the sensor with electric power; a RAM for storing the data; a compression unit for compressing the data stored in the RAM when the wireless communication unit cannot carry out the transmission; and a flash memory for storing the compressed data, thereby storing as much sensing data as possible on the sensor node, which is limited in resources, and preventing loss of the sensing data.

15 Claims, 23 Drawing Sheets

( RF COMMUNICATION ON )

( RF COMMUNICATION OFF )

| CODE | NUMBER OF BITS | VALUE | CODE | NUMBER OF BITS | VALUE |
|---|---|---|---|---|---|
| 1000 | 4 | 0 | 1100 | 4 | -0 |
| 1001 | 4 | 1 | 1111 | 4 | -1 |
| 1010 | 4 | 2 | 1110 | 4 | -2 |
| 1011 | 4 | 3 | 1101 | 4 | -3 |
| 01000 | 5 | 4 | 01100 | 5 | -4 |
| 01001 | 5 | 5 | 01111 | 5 | -5 |
| 01010 | 5 | 6 | 01110 | 5 | -6 |
| 01011 | 5 | 7 | 01101 | 5 | -7 |
| ... | ... | ... | ... | ... | ... |
| 0000000000000 001010 | 19 | 62 | 0000000000000 001110 | 19 | -62 |
| 0000000000000 001011 | 19 | 63 | 0000000000000 001101 | 19 | -63 |
| 0000000000000 00010000000 | 24 | 64 | 0000000000000 00011000000 | 24 | -64 |
| 0000000000000 00010000001 | 24 | 65 | 0000000000000 00011111111 | 24 | -65 |
| ... | ... | ... | ... | ... | ... |
| 0000000000000 00010111111 | 24 | 127 | 0000000000000 00011000001 | 24 | -127 |

| CODE | NUMBER OF BITS | VALUE |
|---|---|---|
| 11000000 | 8 | 0. 0, 0, 0 |
| 11000001 | 8 | 0, 0, 0, 0, 0 |
| 11000010 | 8 | 0, 0, 0, 0, 0, 0 |
| ... | ... | ... |
| 11001111 | 8 | (19 0'S) |

*FIG. 16*

COMPRESSION RATIO

| | |
|---|---|
| RESTING | 12.4% |
| WORKING AT DESK | 33.7% |
| RUNNING | 60.0% |

SENSOR NODE AND SENSOR NETWORK SYSTEM

CLAIM OF PRIORITY

The present application claims priority from Japanese application P2007-158474 filed on Jun. 15, 2007, the content of which is hereby incorporated by reference into this application.

BACKGROUND OF THE INVENTION

This invention relates to a storage for large volume waveform data and a data compression technology for the waveform data used for a compact wireless biological information terminal, and the like.

Recently, for medical practices, health management, and the like at hospitals, nursing and care facilities, and households, terminals which wirelessly receive information from biological information sensors (sensors for sensing ECG, pulse, blood pressure, acceleration, and the like) have been developed.

For example, JP 2005-352881A discloses a behavior management system which measures changes in position and posture of respective parts of a body based on sensors attached to the respective parts of the body, and transmits the measured data via a wireless communication device attached to the body.

Moreover, JP 2006-520657A discloses a system in which a medical wireless terminal with a physiological sensor worn on a body measures biological information, and wirelessly transmits the measured data and a gateway device receives the transmitted data and relays the data by the transmission via the Internet to clinical organizations.

Further, Japanese Patent Translation Publication No. 2005-514138 discloses a system in which a medical terminal worn on a body of a patient measures a health state of the user, generates clinical and medical information, and transmits the generated information to a server or the like using a wireless communication, thereby monitoring the patient. Moreover, in the system according to Japanese Patent Translation Publication No. 2005-514138, when the wireless terminal is used out of range, the sensing data is stored in a flash memory compatible with a personal computer (PC), and is collected by the PC.

As a terminal worn on the body for a long period, a compact terminal with low power consumption is needed. Known is a sensor node, which reduces power by an intermittent operation in which the sensor node intermittently starts up, drives a sensor, and wirelessly communicates the result. See, for example, a catalog, "Wireless Sensor Network MOTE-2007", Crossbow Technology, Inc., retrieved from URL: http://www.xbow.jp/mote2dot.pdf on May 1, 2007. This sensor node can be used to build a wireless network which can extend to a wide area based on relay of data in multiple stages while the network attains low power consumption.

SUMMARY OF THE INVENTION

However, when a sensor network system measuring a state of a human body (or a living organism) by a sensor node to monitor a health state and an activity state is built, it is necessary to continuously or almost continuously monitor the states, and to transmit measured data (sensing data). When a wireless communication environment of the sensor node degrades or the transmission of the sensing data is not allowed due to an environment restricting the wireless communication or the like, it is necessary to store the measured sensing data in the sensor node.

However, as a first problem, the above-mentioned conventional compact sensor node has a limit in available electric power, and thus, the availability of the communication extremely frequently changes depending on a radio wave environment and a state of a user. Thus, a technology of a secure transmission to a monitor or a diagnostic device for the purpose of obtaining continuous sensing data is necessary.

Especially, for a compact sensor node, a usable antenna is limited. Assuming the situation where a chip antenna suitable for the downsizing is mounted on a circuit board of a sensor node, the directivity of electrical wave is strongly biased. If a person uses the sensor node under such a condition in daily life, due to a posture of the person or a surrounding environment, the wireless communication frequently fails even at a communicable distance measured along a straight line. Moreover, a person may be out of range in which the wireless communication is available for a long period. In the environment, in order to carry out secure wireless collection of the data continuously measured by the sensor node, a multi-hop technology in which data is wirelessly transferred to a destination in multiple stages by means of relay devices, as described in the above-mentioned catalog of Crossbow Technology Inc. is effective. However, considering the cost for mounting the relay devices or the like, it is difficult to use this technology for small-scale applications such as a personal application.

Moreover, there is an environment in which an output of electric wave is not allowed. For example, use of a device emitting electric wave is generally restricted in an airport, on an airplane, and in a hospital. In this case, if the sensor node is intentionally turned off, the collection of the sensing data is simultaneously stopped in a subsequent inactive period.

Therefore, in an environment in which the wireless communication is not available, it is necessary for the sensor node to include a function to temporarily store the sensing data in a memory in order to transmit later at once data acquired in the period in which the wireless communication has not been available.

However, in order to carry out even the temporary storage of the data for a long period, a memory which has a large capacity and adapts to a frequent rewrite is indispensable. Therefore, electric power consumption of the memory mounted on the sensor node is important. For example, a flash memory is a high-capacity and inexpensive non-volatile memory. However, if this memory is applied to the sensor node, the flash memory consumes large electric power in the process of rewrite, and a leak current during a standby period is larger than the leak current of a microprocessor during a standby period, which results in a significantly reduced life of a battery used for the sensor node. Thus, a method of rewriting and shutting off a power supply to reduce the power consumption is necessary. JP 2005-352881A, and JP 2006-520657A and JP 2005-514138A disclose the example of an employment of a non-volatile memory such as the flash memory, but the idea of how to reduce the power consumption of the flash memory is not described, reducing the life of the battery on the sensor node.

Moreover, there is another problem in that the service life of the flash memory mounted on the sensor node. There is a limit in the number of the rewrites of the flash memory, and the flash memory cannot be used for a long period, if rewriting is frequently executed. Moreover, the memory mounted on a compact sensor node has a large capacity, but the memory is limited in terms of size and cost. Thus, it is difficult to simply mount the flash memory generally used for the PC. Therefore, even for the temporary storage, it is conceivable to increase the efficiency by compressing the sensing data.

A second problem lies in a limited arithmetic processing capability of a controller (microcomputer) of the sensor node. The microcomputer mounted on the sensor node is much inferior to a CPU mounted on the personal computer in processing capability, so, if a conventional data compression method is applied, the process takes a long period of time, resulting in a large increase in power consumption. For example, as described in JP 2006-520657A, the data compression by means of a conventional method is proposed, but there arises a problem of the significantly reduced battery life on the sensor node. Moreover, the data compression is carried out each time for a radio frequency (RF) packet of approximately 100 bytes, which is smaller than data files handled on a PC, and thus, applicable compression methods are limited. Therefore, a simple but highly efficient compression method is indispensable.

Especially, since JP 2005-352881A and JP 2005-514138A provide the configuration in which the sensing data is directly stored in the flash memory, a high-capacity flash memory is necessary for a period during which wireless communication is not available. Thus, the life of the battery on the sensor node is shorten. Also, when the measurement is continuously carried out, a large amount of the sensing data is written to the flash memory, and thus, the number of rewrites increases. Consequently, the service life of the flash memory is shorten.

In order to solve the above-mentioned problems, the present invention has an object to store as much sensing data as possible in a sensor node, which is limited in resources, thereby preventing loss of the sensing data acquired in a period in which wireless communication is not available, and also to prevent power consumption of a non-volatile memory which stores the sensing data. It is another object of this invention to extend a service life of a non-volatile memory used for storing the sensing data.

According to the present invention, there is provided a sensor node including: a sensor for measuring biological information; a control unit for acquiring data by driving the sensor; a wireless communication unit for transmitting the data acquired by the control unit; a battery for supplying the control unit, the wireless communication unit, and the sensor with electric power; a volatile storage unit for storing the data; a compression unit for compressing the data stored in the volatile storage unit when the wireless communication unit cannot carry out the transmission; and a non-volatile storage unit for storing the compressed data.

The control unit includes a switch for starting, upon start of an access to the non-volatile storage unit, supplying the non-volatile storage unit with the electric power, and stopping, upon end of the access to the non-volatile storage unit, supplying the non-volatile storage unit with the electric power.

The compression unit includes: a difference-representation conversion unit for converting the data into a difference between the data; and an encoding unit for converting the difference into a predetermined variable length code.

The non-volatile storage unit includes a plurality of pages each of which is a predetermined unit of write, and the control unit, upon write of data to the non-volatile storage unit, successively switches the plurality of pages while circulating from a top page toward an end page.

According to this invention, it is possible to surely collect the sensing data for a long period without any loss by compressing and then storing the sensing data, which cannot be wirelessly transmitted, in the non-volatile storage unit.

Moreover, since the electric power is supplied to the non-volatile storage unit only when an access thereto is carried out, it is possible to prevent a leak current or the like in a standby state, thereby preventing the battery from being consumed.

Moreover, the data compression is carried out by obtaining a difference between data, and then, encoding the difference. Biological information (such as acceleration), which is activity data of a living organism, does not exhibit a sudden temporal change, and mostly represents inactivity information, namely a difference of zero, throughout the day, and thus, smaller differences occur more frequently. Then, by encoding the data converted into the difference representation, it is possible to hold more data on the sensor node, and it is thus possible to prevent loss of the sensing data even when a state in which the wireless communication is not available continues.

Moreover, when data is written to the non-volatile storage unit, by successively switching the pages while circulating from the top page toward the end page, it is possible to equalize the write frequency for the respective pages in the non-volatile storage unit, thereby preventing a concentrated rewriting on specific pages to extend service life of the non-volatile storage unit.

BRIEF DESCRIPTION OF THE DRAWINGS

FIG. 16 is a code table illustrating a correspondence between a value and a code for encoding according to the first embodiment.

DETAILED DESCRIPTION OF THE PREFERRED EMBODIMENTS

A description will now be given of embodiments of this invention with reference to accompanying drawings.

First Embodiment

Figure 1:
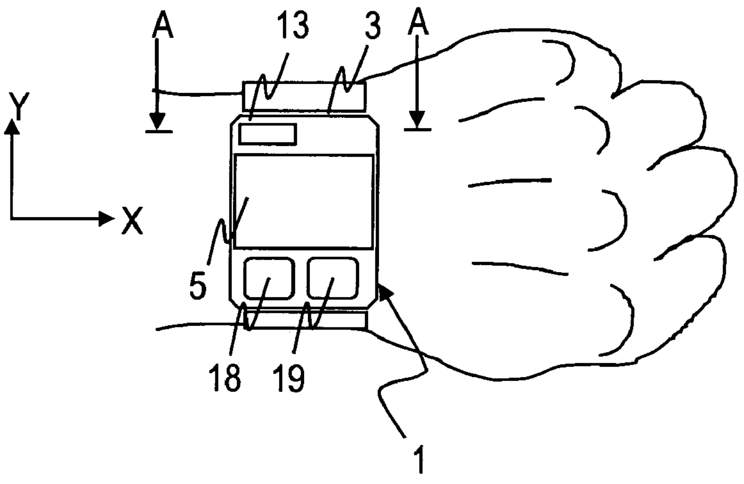
FIG. 1 is a front view of a sensor node of a bracelet type according to a first embodiment of this invention.
Figure 2:
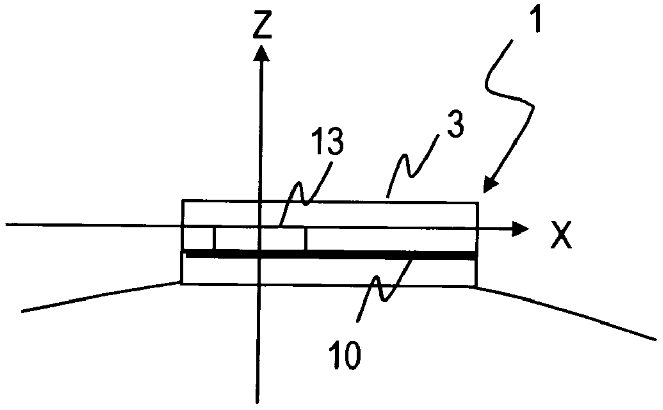
FIG. 2 is a cross sectional view of the sensor node according to the first embodiment made in a direction and on a plane indicated by arrows A of FIG. 1.

FIG. 1 illustrates a first embodiment, and is a front view of a sensor node 1 of a wrist watch (or bracelet) type, to which this invention is applied, and FIG. 2 is a cross sectional view made on a plane and in a direction indicated by arrows A in FIG. 1.

In FIG. 1, the sensor node 1 includes a case 3 which stores an antenna 13, a sensor, and a control unit, and a band used for wearing the case 3 on the arm of the human body. On the case 3, a liquid crystal display (LCD) 5 used for displaying information, and button switches 18 and 19 used for executing specific functions programmed in advance are provided. Moreover, the LCD 5 can be configured as a touch panel for selecting items displayed on the LCD 5. The antenna 13 is shown in FIG. 1 for illustrating a position thereof, but actually, the antenna 13 is arranged on a circuit board 10 disposed inside the case 3 as shown in FIG. 2. In FIG. 2, a surface of the circuit board 10 on which the antenna 13 is mounted is the opposite side of a surface of a living organism, and is the same side as the LCD 5.

The following description is given of a case in which, as a sensor mounted on the sensor node 1 for measuring biological information, an acceleration sensor for measuring each of accelerations along three axes of X, Y, and Z is employed.

Figure 3:
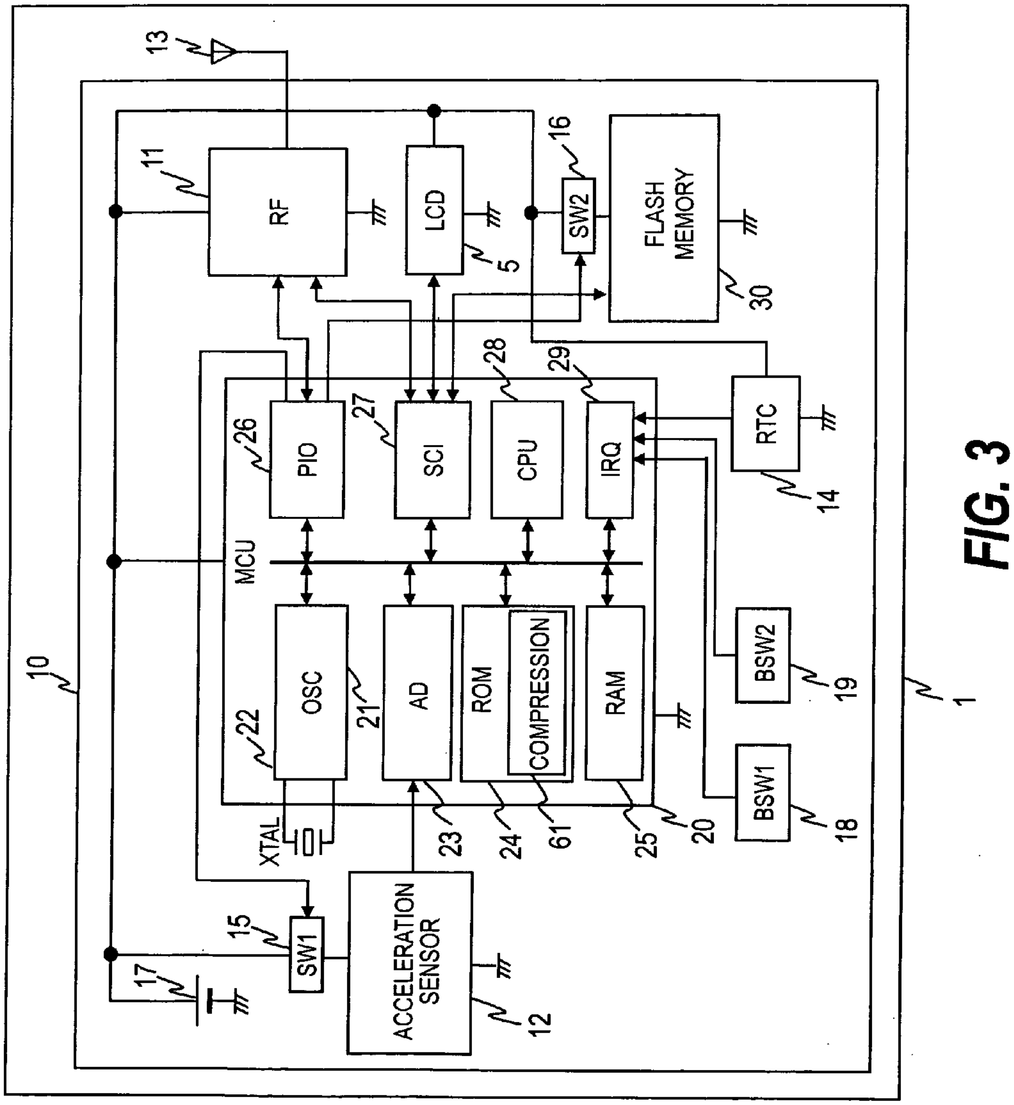
FIG. 3 is a block diagram of the sensor node according to the first embodiment.

FIG. 3 illustrates a block diagram of an electronic circuit mounted on the circuit board 10 of the sensor node 1. In FIG. 3, on the circuit board 10, a radio frequency (RF) communication unit 11 provided with the antenna 13 for communication with a gateway 40 described below, an acceleration sensor 12 which measures the accelerations as the biological information, a microcomputer 20 which controls the acceleration sensor 12 and the radio frequency communication unit 11, a real time clock (RTC) 14 which serves as a timer and clock for periodically starting up the microcomputer 20, a battery 17 which supplies respective units with electric power, a flash memory 30 which is a rewritable non-volatile memory, the LCD 5 which displays characters and waveforms, a switch 15 which controls the electric power supplied to the acceleration sensor 12, a switch 16 which controls the electric power supplied to the flash memory 30, and the button switches 18 and 19 which interrupt the microcomputer 20 to cause the microcomputer 20 to carry out specific processes are provided.

The microcomputer 20 includes a CPU 28 which carries out arithmetic processes, a ROM 24 which is non-volatile memory, and stores programs and the like executed by the CPU 28, a RAM 25 which is configured of a volatile memory for storing data and the like, an interrupt request (IRQ) control unit 29 which interrupts the CPU 28 based on a signal (timer interrupt) from the RTC 14, an A/D converter 23 which converts an analog signal output from the sensor 12 into a digital signal, a serial communication interface (SCI) 27 which transmits and receives serial signals to and from the RF communication unit 11, the flash memory 30, and the like, a parallel input/output (PIO) interface 26 which controls the RF communication unit 11 and the switches 15 and 16, and an oscillation (OSC) unit 22 which supplies the respective units in the microcomputer 20 with a clock. Then, the respective units in the microcomputer 20 are coupled with each other via a system bus 21.

The ROM 24 stores a compression program 61 which compresses the sensor data to reduce the size thereof. The compression program 61 is read out and executed by the CPU 28.

Figure 9:
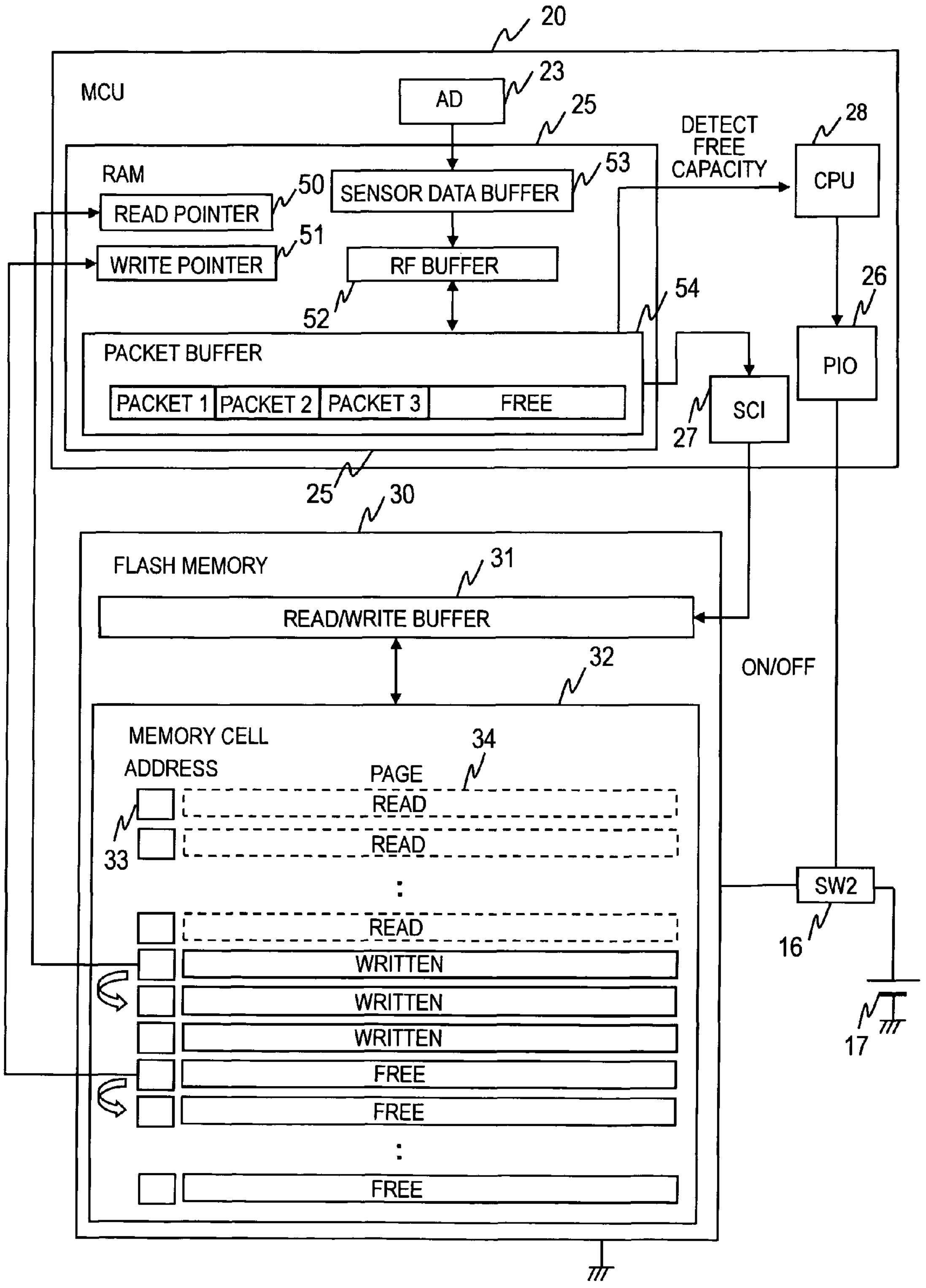
FIG. 9 is a detailed block diagram of a RAM and a flash memory according to the first embodiment.

The flash memory 30, as shown in FIG. 9, includes a memory cell 32 which is a non-volatile storage unit, and a read/write buffer 31 which is a volatile storage unit, and temporarily stores data to be written to (or read from) the memory cell 32. The supply of the electric power to the flash memory 30 can be shut off by the switch 16.

Figure 4:
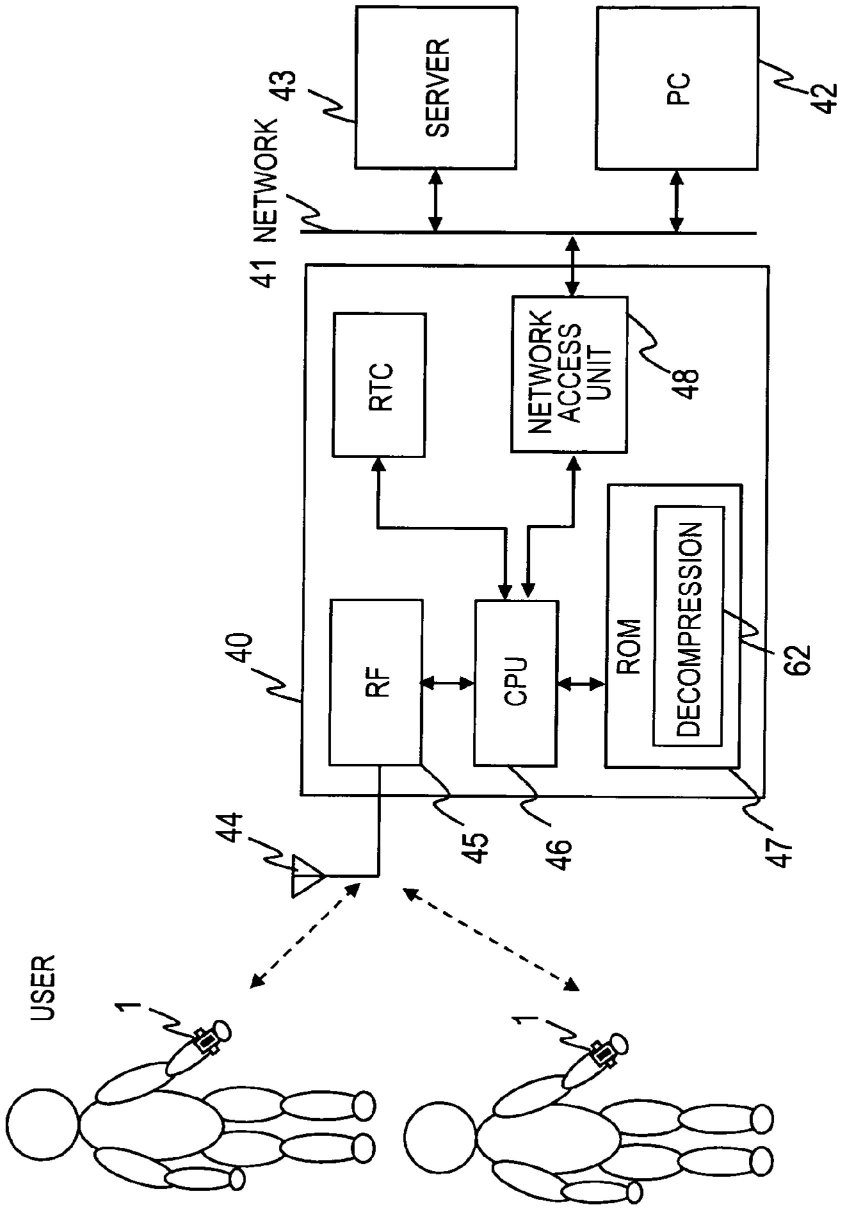
FIG. 4 is a block diagram of a sensor network system according to the first embodiment.

FIG. 4 is a system configuration diagram illustrating an example in which a sensor network system is constructed using the bracelet-type sensor nodes 1 according to this invention.

In FIG. 4, the gateway 40, which serves as a base station or a relay apparatus, communicates with a plurality of sensor nodes 1 via an antenna 44 and an RF communication unit 45. The sensor node 1 transmits a time synchronization request upon a start of the communication. This request is transmitted in order to set a time of the RTC 14 inside the respective sensor nodes 1 to a correct time, thereby attaching a timestamp to sensing data. When the gateway 40 receives the time synchronization request from the sensor node 1, the request is transmitted to the CPU 46 via the RF communication unit 45, and the CPU 46 receives the correct time information from the RTC 49, and transmits the correct time information to the sensor node 1 via the RF communication unit 45. The sensor node 1 sets the time information received from the gateway 40 as a correct time to the RTC 14.

The gateway 40 receives RF packet data including the sensing data according to a motion of a wearer from the respective sensor nodes 1. If the sensing data of the received RF packet data is compressed, the CPU 46 calls a decompression program 62 from the ROM 47 thereby decompressing the sensing data, and if the sensing data is not compressed, the CPU 46 directly transmits the received RF packet data to the network access unit 48, thereby transferring the RF packet data to the server 43 via the network 41.

The server 43 stores the received sensing data or the sensing data extracted from the RF packet data, and provides the sensing data according to a request received from a computer (PC) 42 used by a client. Therefore, the server 43 includes a communication unit which communicates with the gateway 40, a processor (CPU) which carries out arithmetic processes, a memory which stores programs and the like, and a storage unit which stores the sensing data.

Conversely, the server 43 or the PC 42 can transmit an arbitrary command to the sensor node 1, thereby causing the sensor node 1 to execute the arbitrary command. For example, a command can cause the sensor node 1 to change a sensing period and an RF frequency thereof, or the like. In this case, a command is transmitted from the network to the RF communication unit 45 via the network access unit 48 of the gateway 40. When the RF communication unit 45 receives a data transmission request from a sensor node 1, the RF communication unit 45 transmits a command to the sensor node 1. The sensor node 1 carries out what is instructed by the command.

Figure 5:
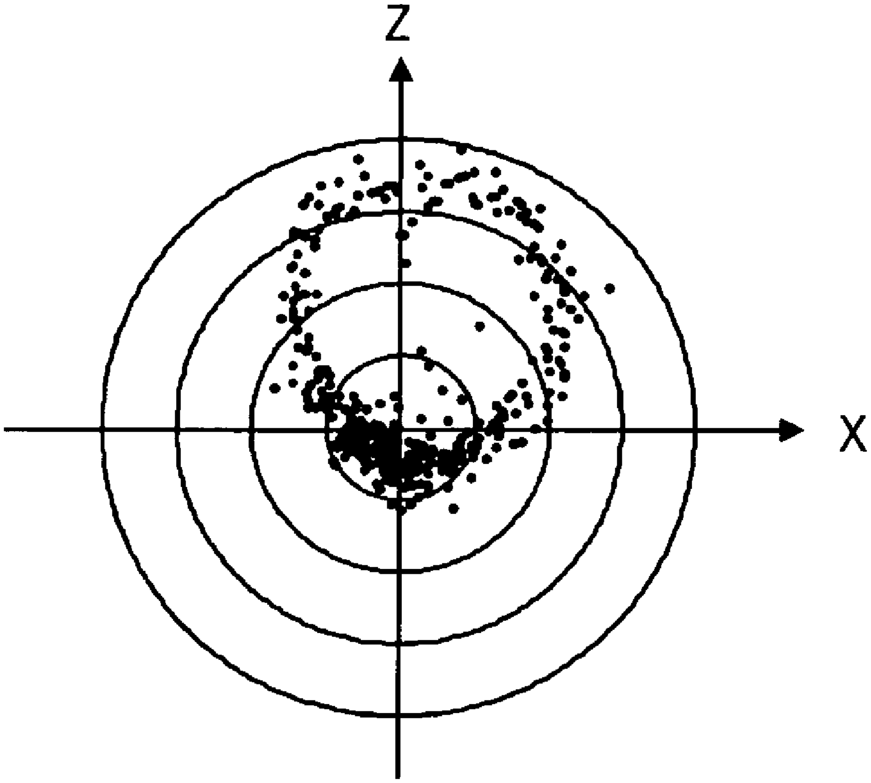
FIG. 5 is a graph illustrating a directivity of a radio wave output of the sensor node on a X-Z plane according to the first embodiment.

FIG. 5 is a directivity of a radio wave output when the antenna 13 is disposed inside the case 3, and the sensor node 1 is worn on the wrist as shown in FIG. 2. The directivity shown in FIG. 5 is high on the opposite side of the living organism surface (upper side on the Z axis of FIG. 5), and largely decreases toward the living organism surface (lower side on the Z axis). In other words, in a daily life of a person, the direction of the body and the arm frequently is changed according to motions, so the directivity is not always high to the direction of the gateway 40, which is a destination of the transmission. Therefore, if the sensor node 1 is used in the daily life, it is inferred that an intensity of the electric wave received at the destination of transmission is low, or the reception is highly possibly fails.

Figure 6:
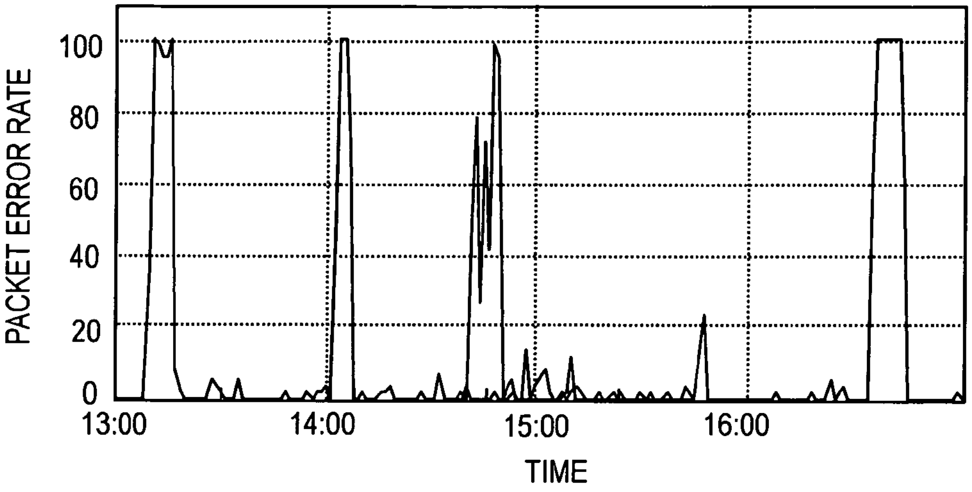
FIG. 6 is a graph illustrating a packet error rate when the sensor node transmitted packets according to the first embodiment.

FIG. 6 illustrates a packet error rate (failed number of wireless transmissions/total number of wireless transmissions) when the sensor node 1 shown in FIG. 1 was worn on the arm, and was actually used in a general household. The gateway 40 was placed at a center portion of the household (area of a center portion of the household is approximately 50 $m^2$), and a user stayed on the same floor as the gateway 40. In this case, the user stayed within a communicable distance which is 50 meters measured along a straight line from the gateway 40, but packet errors frequently occurred. It is considered that this is caused not only by the directivity of the radio wave shown in FIG. 5, and by motions of the user but also by strong influence of radio wave interferences generated by radio wave appliances such as a wireless LAN and a microwave oven which use the same frequency. In other words, this case illustrates that, when a sensor node which is powered by a small battery and, thus, provides a low power for the RF communication is used in the real environment, the RF communication fails frequently regardless of the communication distance.

Thus, according to this invention, the sensor node 1 is provided with the flash memory 30 as storage means which can be frequently rewritten, and has a large capacity, has a function which temporarily stores RF packet data in the flash memory 30 when the radio wave condition is unfavorable, or the RF communication unit 11 is turned off, and transmits at once the sensing data stored in the flash memory 30 when the radio wave condition is favorable, or the RF communication unit 11 is turned on.

Figure 7:
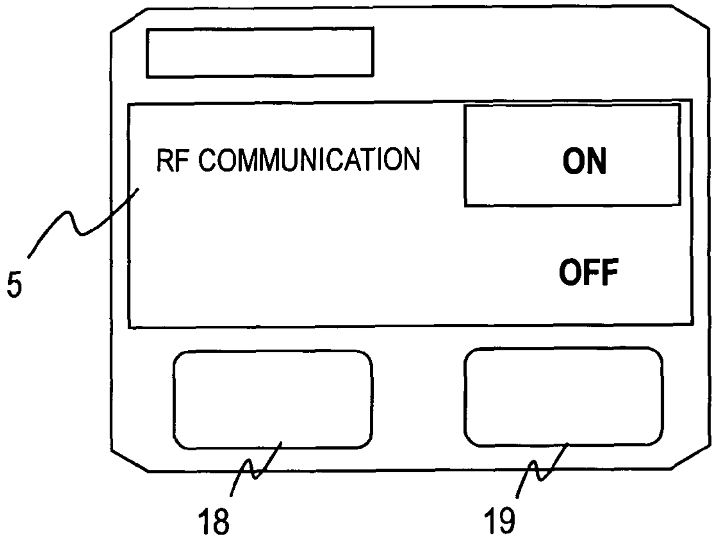
FIG. 7 illustrates an example of a display shown on an LCD of the sensor node in a state in which a radio frequency communication unit is on according to the first embodiment.
Figure 8:
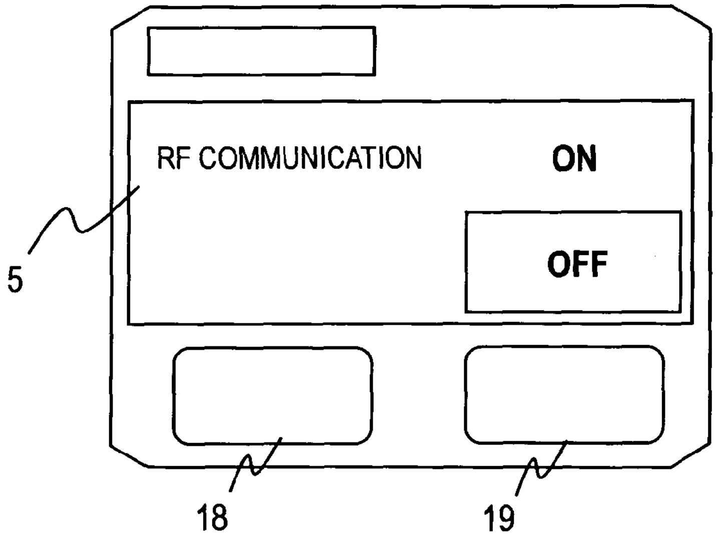
FIG. 8 illustrates an example of the display shown on the LCD of the sensor node in a state in which the radio frequency communication unit is off according to the first embodiment

Moreover, when the use of wireless units is restricted, it is possible, as shown in FIG. 8, to turn off (or on) only the RF communication unit 11 by operating the sensor node 1 with the button switches 18 and 19. While the RF communication unit 11 is turned off, the sensing by the acceleration sensor 12 continues, but RF packet data cannot be transmitted, so, the RF packet data are stored in the internal memory (the RAM 25 or the flash memory 30). If the RF communication unit 11 is turned off, as shown in FIG. 8, on the LCD 5, appears a display indicating that the RF communication unit 11 is off. The packet data stored in the memory are transmitted at once when the restriction on the use of wireless units no longer exists and after the RF communication unit 11 is turned on. It should be noted that, on the sensor node 1, the RF communication unit 11 can be turned on by carrying out a predetermined operation on the button switches 18 and 19. When the RF communication unit 11 is turned on, as shown in FIG. 7, on the LCD 5, appears a display indicating that the RF communication unit 11 is on.

FIG. 9 is a block diagram describing control to store and load RF packet data to and from the RAM 25 and the flash memory 30 in order to realize the function which temporarily stores the RF packet data in the flash memory 30 when the radio wave condition is unfavorable or the user turns off the RF communication unit 11.

In the RAM 25 in the microcomputer 20 of the sensor node 1, there are set a sensor data buffer 53 for temporarily storing sensing data output by the A/D converter 23, an RF buffer 52 for storing RF packet data to be transmitted and other data, a packet buffer 54 for temporarily storing sensing data to be written to the flash memory 30, a read pointer 50 for indicating a position to read from the flash memory 30, and a write pointer 51 for indicating a position to write to the flash memory 30.

The sensing data measured by the acceleration sensor 12 is once stored in the sensor data buffer 53, the CPU 28, on a transmission timing of the sensing data, generates RF packet data in a predetermined format from the sensing data read form the sensor data buffer 53, and stores the RF packet data in the RF buffer 52. Then, if the RF communication is available, the CPU 28 reads the RF packet data from the RF buffer 52, and transmits the RF packet data from the RF communication unit 11 to the gateway 40.

On the other hand, in an environment where the RF communication is not available, the CPU 28 compresses the sensing data of the RF packet data read from the RF buffer 52 by conversion into difference representation, and encoding, which are described below, and accumulates the compressed sensing data in the packet buffer 54 in the RAM 25. For example, when the minimum write unit (hereinafter, referred to as page) of the flash memory 30 is 1 kilobytes, the read/write buffer 31 of the flash memory 30 and the packet buffer 54 of the RAM 25 preferably have the same or less capacity. When the read/write buffer 31 and the packet buffer 54 have the same capacity, and the size of one RF packet data is 100 bytes, ten of the RF packet data can be accumulated in the packet buffer 54. Moreover, if the RF packet data contains compressed sensing data, more RF packet data can be accumulated in the packet buffer 54. While the power consumption of the flash memory 30 is high for the write operation, the RAM 25 is rewritten at a high speed, and with low power consumption, and is thus suitable for reading and writing RF packet data when the radio wave condition frequently changes.

Then, when the free capacity of the packet buffer 54 is a size of one packet or less, or when unsent data exists in the flash memory 30, and unsent data (RF packet data) in the packet buffer 54 is one packet, an access to the flash memory 30 is necessary, and thus, the CPU 28 controls the parallel interface 26 to turn on the switch 16 in advance, which has turned off the power supply to the flash memory 30. This start up of the flash memory 30 requires a wait time of some milliseconds.

Then, when the accumulated quantity of the RF packet data reaches the limit of the packet buffer 54, the RF packet data is transferred to the read/write buffer 31 of the flash memory 30 via the serial communication interface 27 by the serial communication, and is written to a page 34 of the memory cell 32. After the write operation, the CPU 28 again controls the parallel interface 26 to turn off the switch 16, thereby shutting off a leak current during the standby of the flash memory 30.

Conversely, when all the RF packet data in the packet buffer 54 are transmitted, the CPU 28 reads unsent RF packet data form a page 34 of the memory cell 32 of the flash memory 30 to the read/write buffer 31 via the serial communication interface 27, receives the RF packet data by means of the serial communication, and writes the RF packet data on the packet buffer 54. After the RF packet data has been read, the CPU 28 again controls the parallel interface 26 to turn off the switch 16. In other words, by stopping the power supply to the flash memory 30 while the write operation is not being carried out, the battery 17 can be prevented from being consumed.

A read address and a write address of the page addresses 33 of the pages 34 of the flash memory 30 are stored in the RAM 25 as the read pointer 50 and the write pointer 51, respectively, thereby efficiently reducing the number of the rewrite operations on the flash memory 30.

Respective initial values of the read pointer 50 and the write pointer 51 are the top address of the memory cell 32, and, when there are no unsent RF packet data in the flash memory 30, the values of the read pointer 50 and the write pointer 51 are the same. The CPU 28 increments the value of the write pointer 51 by one each time RF packet data is written to a page 34, and the read operation is carried out at an address pointed by the read pointer 50. Each time a page 34 is read, the CPU 28 also increments the read pointer 50 by one, and stores the incremented value. As a result, the rewrite address sequentially circulates from the top address of the memory cell 32, all the frequencies of the rewrite on the respective pages 34 in the memory 32 are almost equated, so the rewrite operation does not concentrate on some of the pages 34.

Figure 10:
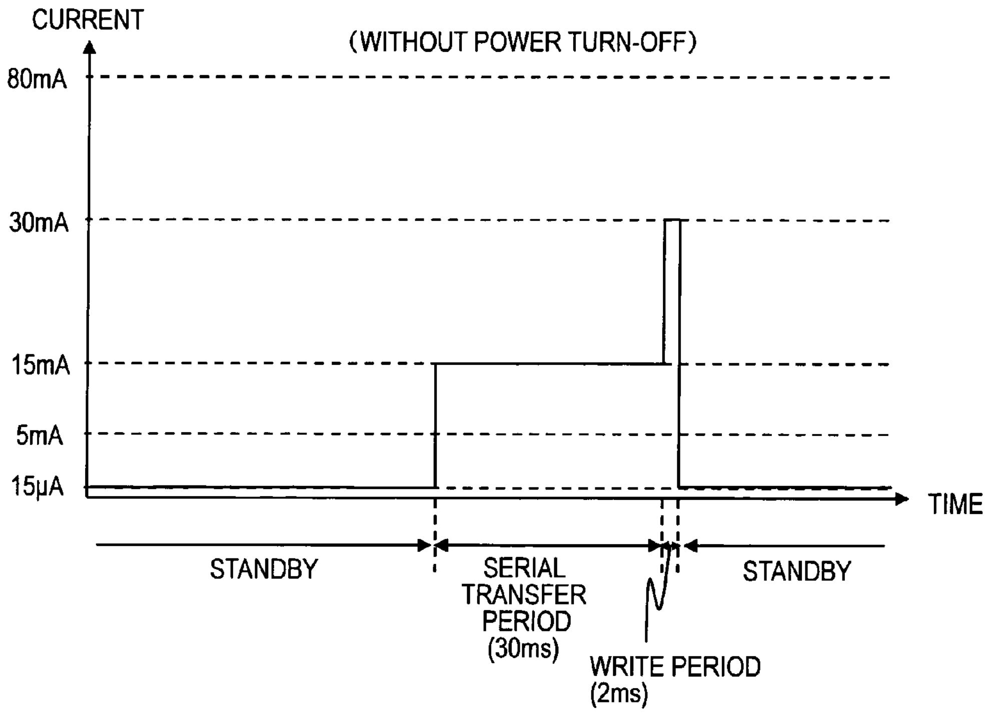
FIG. 10 is a graph illustrating a relationship between power consumption of the flash memory and time without shut-off of a power supply according to a conventional example.
Figure 11:
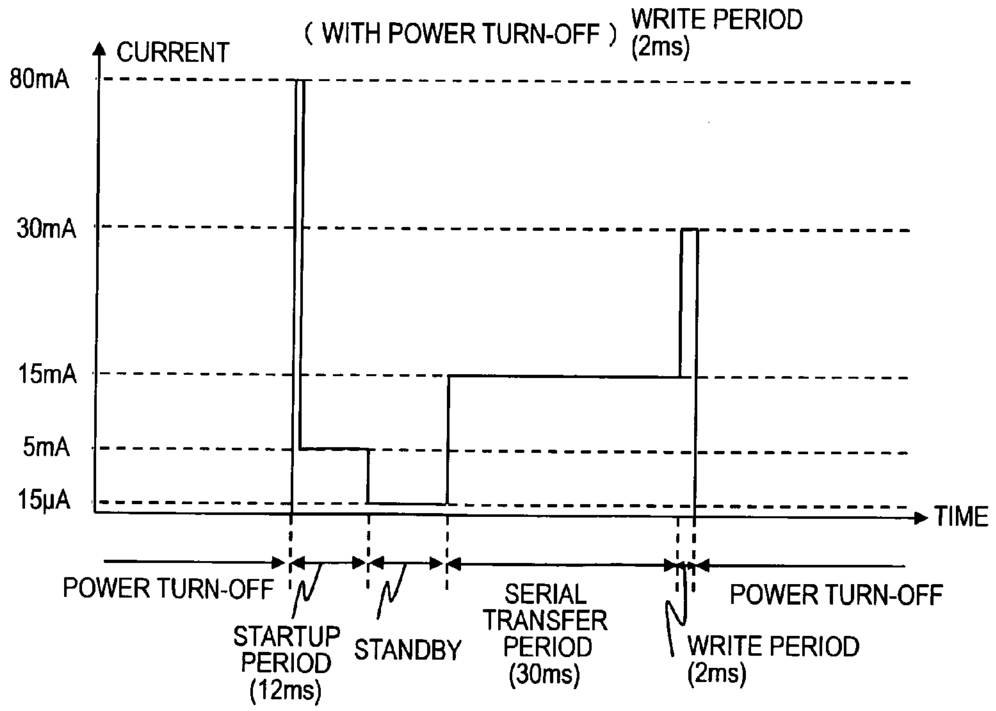
FIG. 11 is a graph illustrating the relationship between the power consumption of the flash memory and time with the shut-off of the power supply according to the first embodiment.

FIGS. 10 and 11 illustrate a typical example of current consumption of the flash memory 30 when data of one kilobytes is written. FIG. 10 illustrates a conventional example in which the power supply to the flash memory 30 is not shut off. FIG. 11 illustrates an example of this invention in which the power supply to the flash memory 30 is shut off.

In FIG. 10, in the case where the power supply is not shut off when the flash memory 30 is out of operation, the flash memory 30 continues consumption of the leak current of 15 μA during the standby state. However, during the standby state the serial communication or the data write can be immediately carried out, and can be finished in approximately 30 milliseconds as shown in FIG. 10.

On the other hand, in the case where the power supply is shut off when the flash memory 30 is out of operation, as shown in FIG. 11, a startup period (approximately 12 milliseconds) is necessary when the power supply is turned on, and the current consumption is 80 mA at its peak, and is 5 mA during the rest of the startup period. This peak current is larger than the current during the standby state, but the startup period is only about 12 milliseconds. This corresponds to current consumption for 5 seconds of the standby. Therefore, when data corresponding to ten packets are buffered and the read and write operations are carried out for these ten packets on the flash memory 30, the interval of the startups is at least 10 seconds even for successive read and write operations, and the current consumption and hence, the power consumption are smaller when the power supply is shut off.

Figure 12:
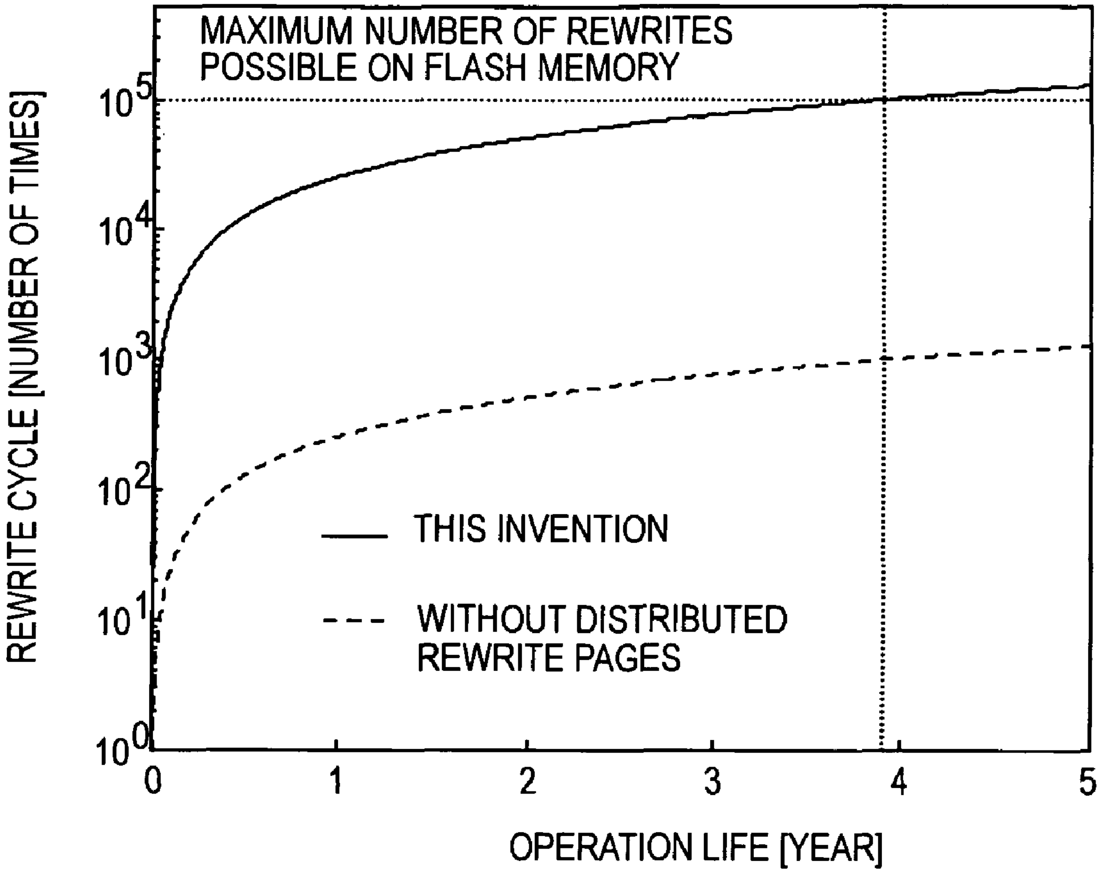
FIG. 12 is a graph illustrating the relationship between the maximum number of rewrites made on the flash memory and time with respect to the maximum possible number of rewrites according to the conventional example and the first embodiment.

FIG. 12 illustrates an effect of the distributed rewritten addresses according to this invention shown in FIG. 9, and compares the number of rewrites on a page 34 with the number of rewrites on the most frequently rewritten page in the case where the sensor node 1 is used in the daily life. According to this invention, the rewrite is not concentrated on specific pages 34, but is almost evenly distributed across all the pages 34, resulting in 1/100 of the rewrite frequency compared with the case without circulating the rewrite address. As a result, it is possible to extend the service life of the flash memory 30 used as the non-volatile memory for storing the RF packet data (sensing data).

Figure 13A:
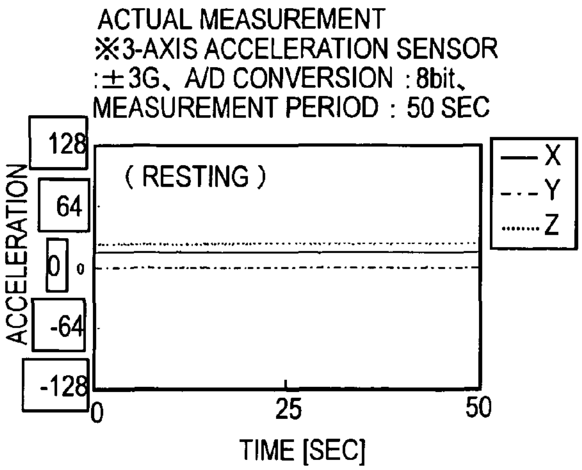
FIG. 13A is a graph illustrating a relationship between actual measurements of accelerations along three axes and time acquired by the sensor node when a resting person was sensed according to the first embodiment.

A description will now be given of a method of compressing sensing data according to this invention. According to this invention, motions of a person whose biological information is measured and characteristics of the data are focused. For example, FIGS. 13 to 15 illustrate data on accelerations (in a range of ±3 G) along the three axes (X, Y, and Z axes) when the sensor node 1 was worn on the arm of a person and the person exhibited typical behaviors (such as resting, working at desk, and running). It should be noted that the resolution of the A/D conversion is eight bits, the sampling frequency is 20 Hz, and the sampling cycle is 50 seconds. FIG. 13A illustrates the accelerations along three axes in a resting state. FIG. 14A illustrates the accelerations along three axes in a state of work at desk. FIG. 15A illustrates the accelerations along three axes in a running state.

Figure 13B:
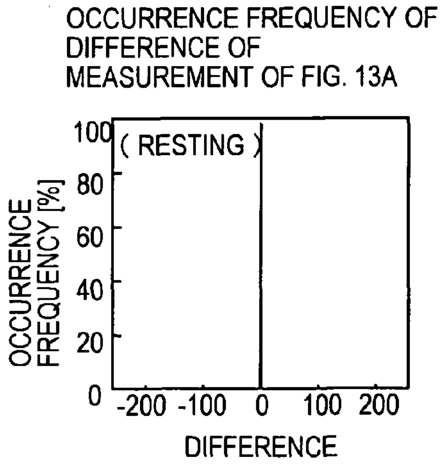
FIG. 13B is a graph illustrating a relationship between an acceleration in a difference representation and an occurrence frequency thereof acquired by the sensor node when a resting person was sensed according to the first embodiment.
Figure 14A:
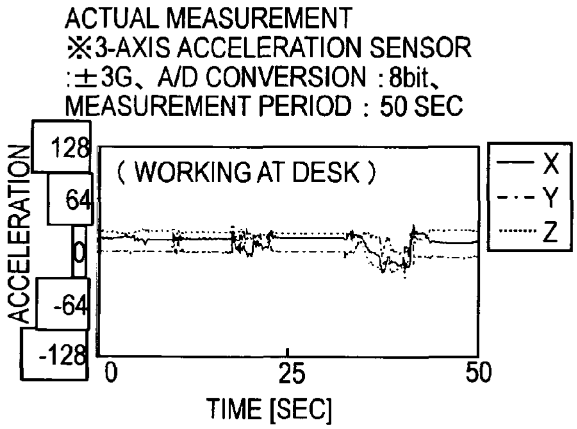
FIG. 14A is a graph illustrating a relationship between actual measurements of accelerations along three axes and time acquired by the sensor node when a person working at desk was sensed according to the first embodiment.
Figure 14B:
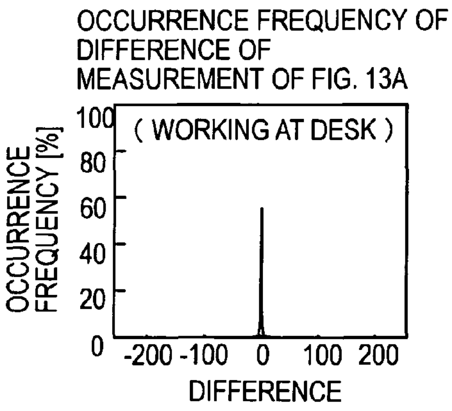
FIG. 14B is a graph illustrating a relationship between an acceleration in the difference representation and an occurrence frequency thereof acquired by the sensor node when a person working at desk was sensed according to the first embodiment.
Figure 15A:
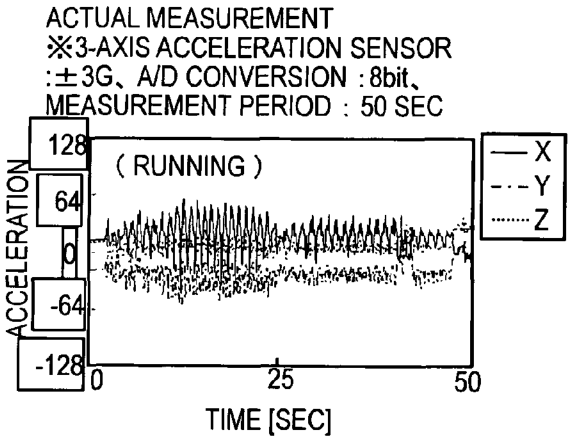
FIG. 15A is a graph illustrating a relationship between actual measurements of accelerations along three axes and time acquired by the sensor node when a running person was sensed according to the first embodiment.
Figure 15B:
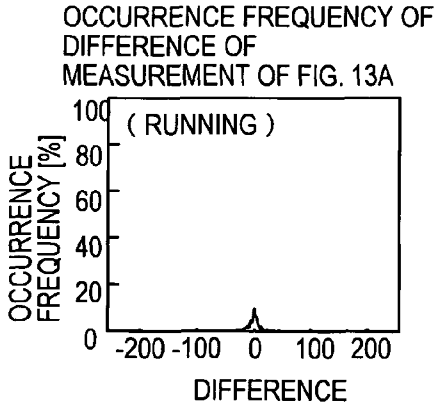
FIG. 15B is a graph illustrating a relationship between acceleration in the difference representation and an occurrence frequency thereof acquired by the sensor node when a running person was sensed according to the first embodiment.

FIGS. 13B, 14B, and 15B illustrate an occurrence frequency of a difference of an actual measurement with respect to a previous measurement of the accelerations shown in FIGS. 13A, 14A, and 15A, respectively. In FIGS. 13 to 15, in the resting state shown in FIG. 13, there are no changes, and the difference of 0 thus occurs at a rate of almost 100%. In the state of working at desk shown in FIG. 14 and in the running state shown in FIG. 15, which is an example of the hardest exercise, it is considered that changes in the accelerations along the three axes increase, resulting in a distributed occurrence frequency of the differences. However, even when the motion of the person exhibited the large changes, the occurrence frequency is higher for smaller differences, and is centered on a range of the difference from zero to a value of one digit. Moreover, considering activities of a person throughout the day, the length of period of resting and sleeping is relatively long, resulting in a very unevenly distributed occurrence frequency of the difference.

Since the occurrence frequency of the difference is centered around zero, by means of a simple encoding as shown in FIGS. 13B to 15B, it is possible to efficiently and reversibly compress the acceleration data in the memory.

A description will now be given of an encoding method according to this invention.

The encoding method according to this invention is a variable-length encoding which assigns a shorter code to a smaller value. FIG. 16 is a table illustrating a variable length code according to this invention. If a number (acceleration) is close to zero, the value represented by eight bits can be compressed to a value represented by four bits which is a half of eight bits. However, as the value increases, the bit length increases accordingly and may exceed eight bits which is the original data length. Moreover, when values are three to nineteen successive 0's, these successive 0's are collectively represented by eight bits. This is because, as shown in FIGS. 13B to 15B, the fact that the difference zero of the acceleration generated by human activity appears most frequently is utilized to increase the efficiency of the compression. When the number of successive zero's is nineteen, 152 bits can be compressed to eight bits.

Figure 17:
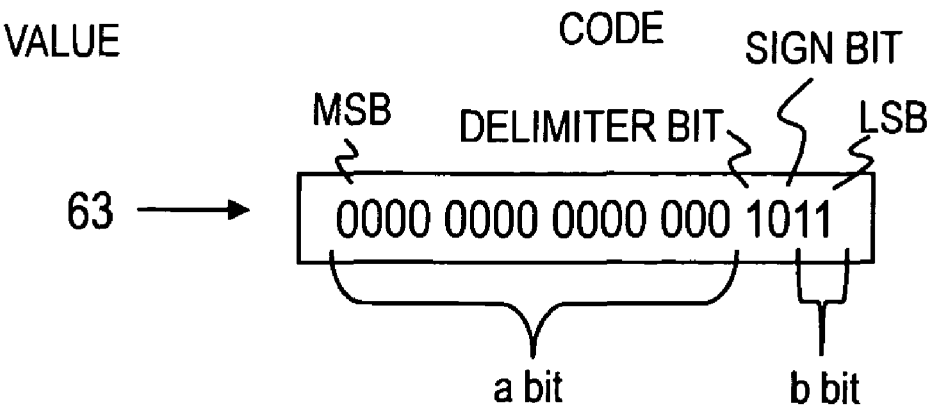
FIG. 17 describes a bitwise configuration of the code according to the first embodiment.

FIG. 17 illustrates a configuration of the variable length code in the case where the sensing data is represented by eight bits. The variable length code is constructed by "a" of bits starting from the most significant bit (MSB), a delimiter bit, a sign bit indicating positive or negative, and "b" bits down to the least significant bit (LSB). The variable length code has different bit configurations in the case of values less than 64 and values equal to or more than 64.

First, when a value is less than 64, the "a" bits are a number of successive zero's, the number being a quotient obtained by dividing the value by four, and the "b" bits represent the remainder of this calculation. It should be noted that "b" bits represent the remainder of division by four, and the "b" bits are thus two bits. The delimiter bit is always one, and the sign bit is zero for a positive number and 1 for a negative number. For example, for a value of four, a quotient and a remainder of the division of the value of four by four are respectively zero and zero, the "a" bit is zero, the MSB is thus the delimiter bit, and the "b" bits are "00".

If a value is 64 or more, the number "a" of zero's is 16, and a difference obtained by subtracting 64 from the value is set to lower six bits as "b" bits. The delimiter bit and the sign bit are the same as the delimiter bit and the sign bit when the value is less than 64. For example, for a value of 65, "a" bits, which is 16 bits, of zero's are set from MSB, and one, which is obtained by subtracting 64 from 65 is set to the lower six bits.

Moreover, as shown in FIG. 16, a code "1100" is not "−0", but is used to represent successive four or more zero's. Thus, as shown in the lower part of FIG. 16, "a" is zero, and, of "b" bits of six bits, lower four bits represent the number of successive four or more zero's. In other words, as shown in FIG. 16, "11000000" represents succession of four zero's, and "11001111" represents succession of 4+15=19 zero's.

Figure 18:
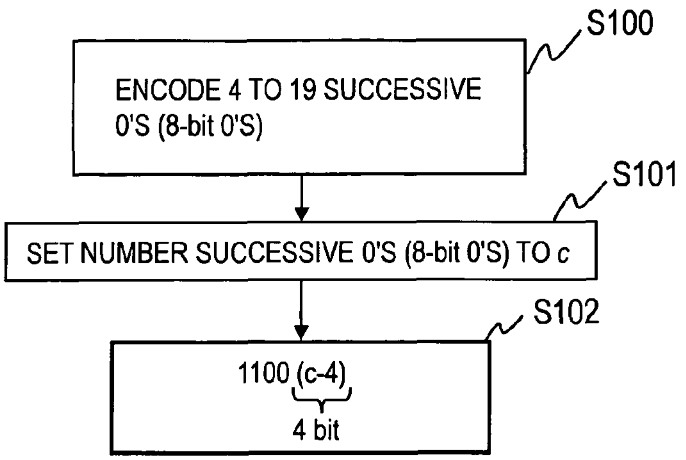
FIG. 18 is a flowchart illustrating an example of an encoding process carried out on the sensor node in a case where successive four or more zero's appear as sensing data according to the first embodiment.
Figure 19:
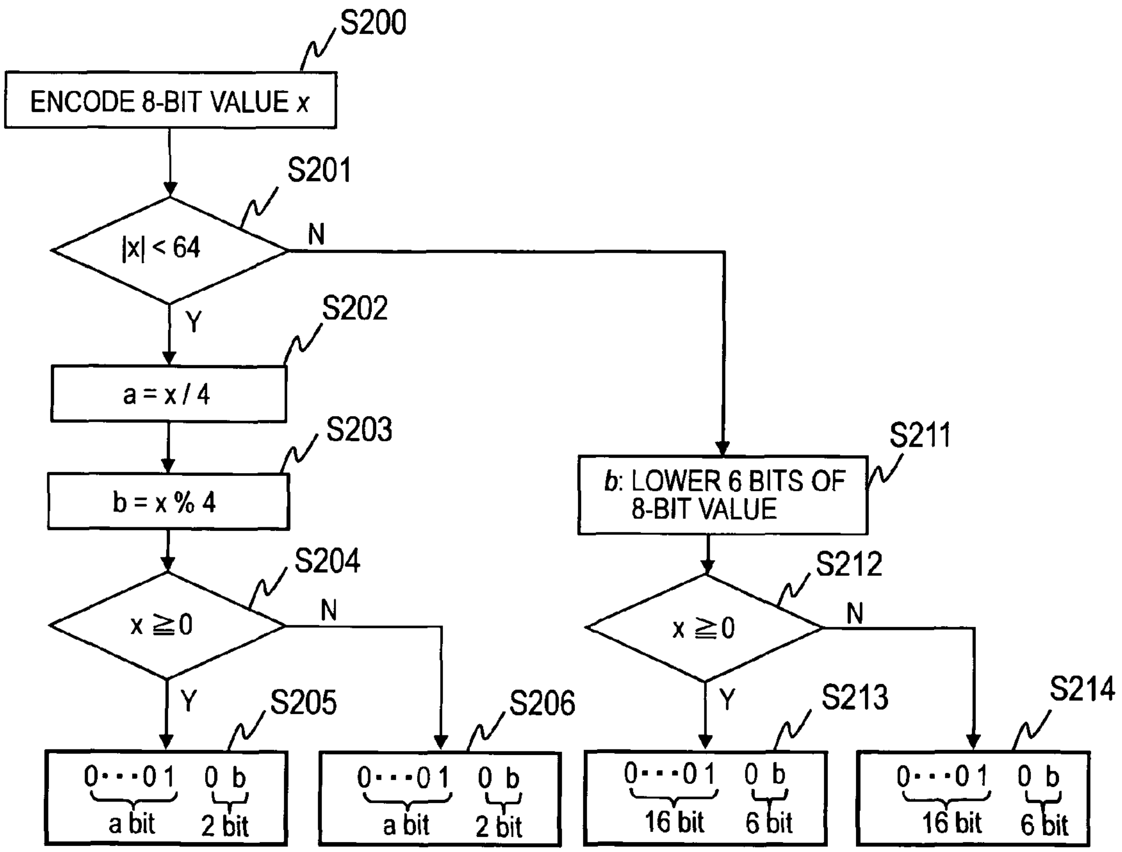
FIG. 19 is a flowchart illustrating an example of an encoding process carried out on the sensor node in a case where sensing data is not 0, or the number of successive zero's is less than four according to the first embodiment.

FIGS. 18 and 19 are flowcharts illustrating a process of encoding a value carried out by the compression program 61 executed by the CPU 28. FIG. 18 illustrates the case where successive zero's are encoded. And FIG. 19 illustrates the case where a value larger than zero or succession of one to three zero's is encoded. It should be noted that the compression program 61 reads the sensing data in the RF packet data from the RF buffer 52 of the RAM 25. Then, when the value of the sensing data is zero, and the number of successive zero's is four or more, the compression program 61 carries out the process shown in FIG. 18. Otherwise, the compression program 61 carries out the process shown in FIG. 19.

In FIG. 18, if the top values of the sensing data to be encoded are four or more successive zero's, the values are encoded at once. The process starts from a step S100, and the CPU 28 counts the number of successive zero's in the sensor data buffer 53, and sets the number to "c" in a step S101.

In a step S102, the CPU 28 sets a value obtained by subtracting four from "c" to the lower four bits as the "b" bits in FIG. 17.

On the other hand, if successive values to be encoded are not successive four or more zero's, one eight-bit value is encoded by the process shown in FIG. 19.

In a step S200, the CPU 28 assigns the value of the sensing data in the sensor buffer 53 to a variable "x".

In a step S201, if the absolute value of the variable "x" is less than 64, the CPU 28 proceeds to a step S202, and the absolute value of the variable "x" is equal to or more than 64, the CPU 28 proceeds to a step S211. In the step S202, the CPU 28 sets a quotient obtained by dividing the variable "x" by four (in other words, x/4) to "a", and, in a step S203, the CPU 28 sets a remainder obtained by dividing the variable "X" by four (X%4) to "b".

In a step S204, if the variable "x"≧0, the CPU 28 proceeds to a step S205. Otherwise, the CPU 28 proceeds to a step S206. In the step S205, since the variable "x" is positive, the CPU 28 sets 0 to the sign bit, sets "a" 0 bits, "a" being assigned the quotient, and sets the remainder to the "b" bits. In the step S206, since the variable "x" is negative, the CPU 28 sets 1 to the sign bit, sets "a" 0 bits and the "b" bits as in the step S205, and completes the encoding.

In the step S211 for the case of the variable x≧64, a value obtained by subtracting 64 from the variable "x" is set to the "b" bits, which are lower six bits shown in FIG. 17.

In a step S212, if the variable "X"≧0, the CPU 28 proceeds to a step S213. Otherwise, the CPU 28 proceeds to a step S214. In the step S213, since the variable "x" is positive, the CPU 28 sets 0 to the sign bit, sets sixteen 0 bits to the "a" bits, and sets the six bits set in the step S211 to the "b" bits. In the step S214, since the variable "x" is negative, the CPU 28 sets 1 to the sign bit, sets "a" of 0 bits and the "b" bits as in the step S213, and completes the encoding.

According to the encoding processes shown in FIGS. 18 and 19, it is not necessary to include information on the encoding table shown in FIG. 17 and the like (dictionaries) in data retained by the sensor node 1, the processes can be mostly carried out as bitwise operations without multiplications, are thus simple arithmetic processes. Therefore, the processes can be carried out at a high speed by the microcomputer 20 of the sensor node 1.

Figure 20:
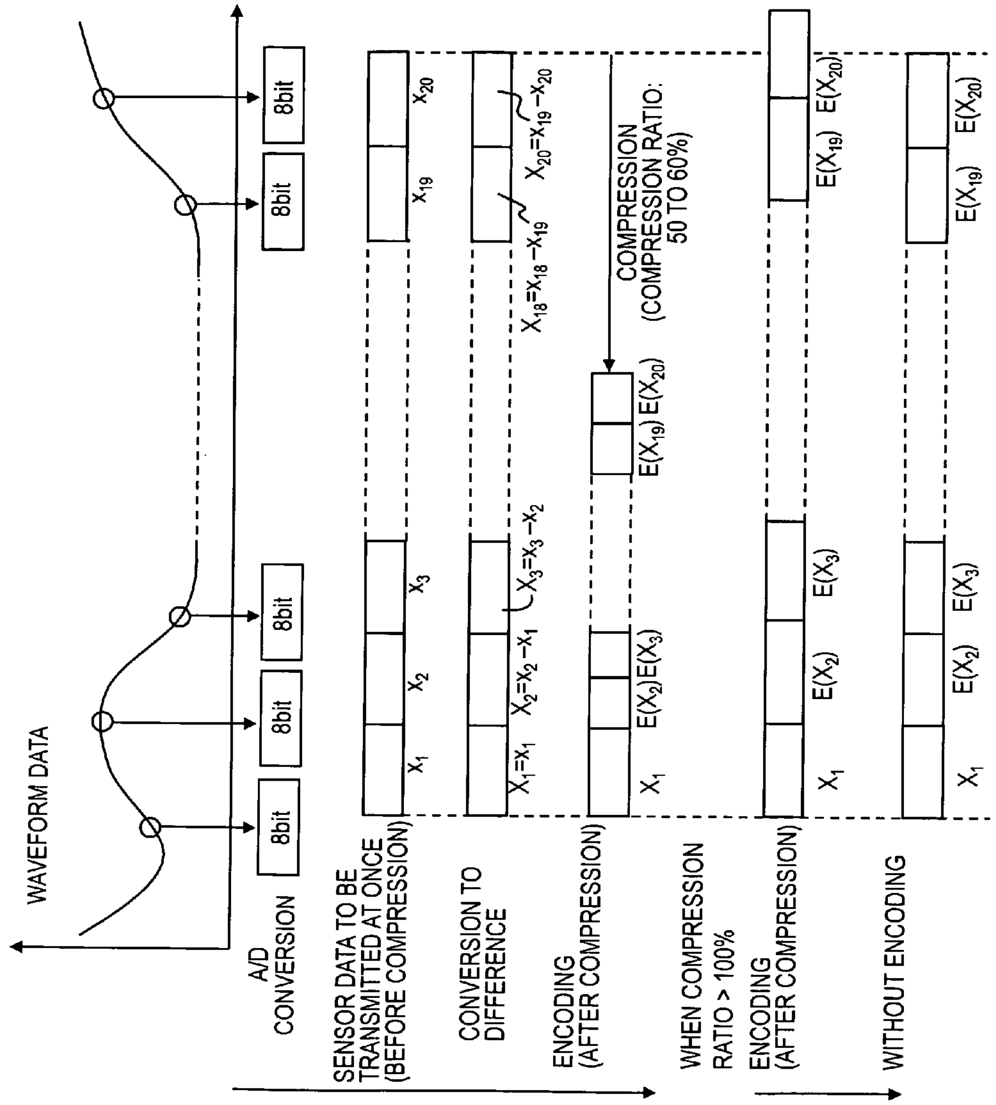
FIG. 20 is an explanatory diagram illustrating a data length brought about by the conversion into the difference representation and by the encoding according to the first embodiment.

FIG. 20 illustrates a process of compressing data, which is obtained by the conversion into the difference representation shown in FIGS. 13 to 15, and the encoding shown in FIG. 16, thereby producing the RF packet data. Biological information (pulse and acceleration, for example) is converted into a numerical value by a sensor, and a voltage which is the output from the sensor is a waveform of an analog value which changes over time.

The sensor node 1 converts the analog value (waveform data of FIG. 20) from the acceleration sensor 12 into a digital value (eight bits, for example) at a constant frequency (20 Hz, for example) by the A/D converter 23 of the microcomputer 20. These digital values sent by the wireless transmission at once (20 of the digital values, for example) are stored in the sensor data buffer 53.

The microcomputer 20 converts these 20 digital values into the difference representation. The process of the conversion into the difference representation uses a value of a first data X1 of the 20 digital values (sensing data), directly, and converts the subsequent data X2 to X20 into differences based on the previous data Xn-1.

These values represented as differences are encoded as shown in FIGS. 18 and 19. However, the variable length code shown in FIG. 16 may have a longer length than the variable length code of original data. In order to prevent compression efficiency from significantly decreasing, non-compressed data is directly used only when the compression ratio exceeds 100%.

As described below, the write to the flash memory 30 is not carried out each time RF packet data which cannot be transmitted is generated, but the CPU 28 carries out the write to the flash memory 30 when the number of RF packet data stored in the packet buffer 54 reaches a predetermined number (20, for example), and deletes the written RF packet data from the packet buffer 54.

In this way, by writing a certain number of RF packet data at once to the flash memory 30, it is possible to reduce the frequency of turning on/off the flash memory 30, and to reduce the period to supply the flash memory 30 with the electric power. As a result, it is possible to prevent the battery 17 from being consumed, thereby increasing the frequency of the maintenance of the sensor node 1 for replacing or charging the battery 17.

Figures 21, 22:
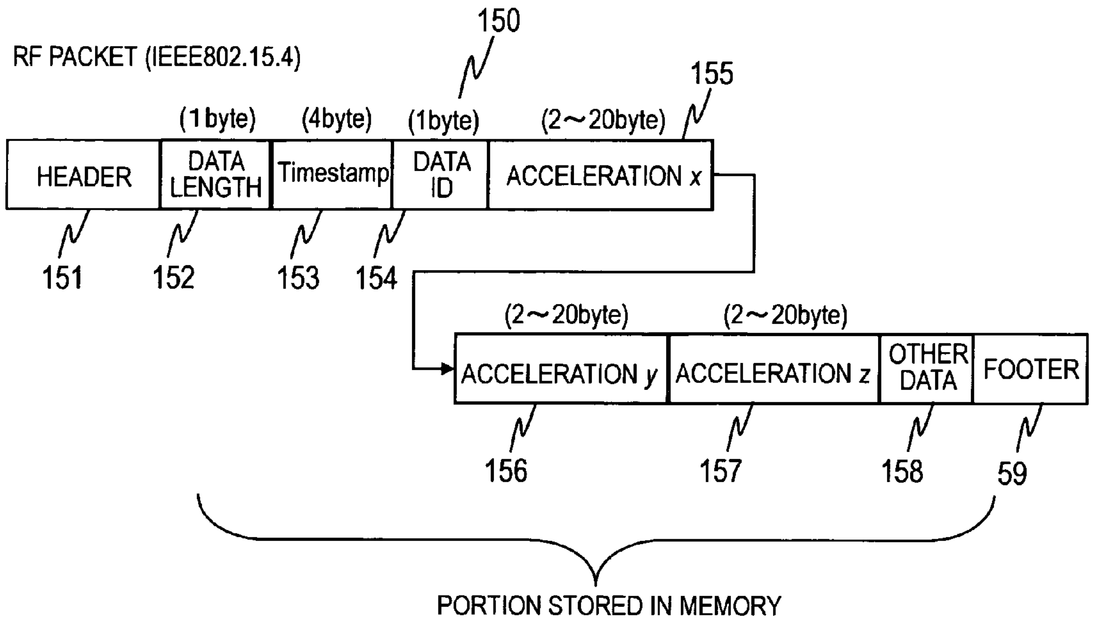
FIG. 21 is a block diagram illustrating a configuration of an RF packet transmitted by the sensor node according to the first embodiment.
FIG. 22 is a table illustrating an example of compression ratios of sensing data brought about by the conversion into the difference representation and by the encoding according to the first embodiment.

FIG. 21 illustrates an example of a format 150 of the RF packet data when the IEEE 802.15.4 is employed as a wireless network standard. According to this format 150, except for a header 151 and a footer 159, a data portion (payload) of approximately 100 bytes stores data. This data portion stores a data length 152 of the data portion (1 byte), a time stamp 153 (4 bytes) which is generated when the packet was produced, a data ID 154 (1 byte) which is used to determine the type of the data, compressed or non-compressed acceleration sensing data 155 (X axis), 156 (Y axis), and 157 (Z axis), and other data 158. With the time stamp 153, even if the order of the transmission of packets is not chronological, original waveform data can be recovered. The data ID 154 indicates a content of the sensing data. The data ID 154 also allows the judgement of the compressed/uncompressed state of the sensing data. As the other data 158, the sampling frequency, the resolution, an emergency message from a user, and the like may be stored in the same packet.

FIG. 22 illustrates compression ratios in the case where 8-bit values which are the actual measurements shown in FIGS. 13 to 15 are compressed into RF packet data according to the procedure shown in FIG. 20. The result illustrates that the measurements in the resting state can be compressed at a compression ratio of 12.4%, which is the most efficient. Even the measurements in the running state, which is an example of the hardest activity, can be compressed at a compression ratio of 60.0%. In a typical one-day example including these activities, a compression ratio of approximately 33% can be achieved.

Figure 23:
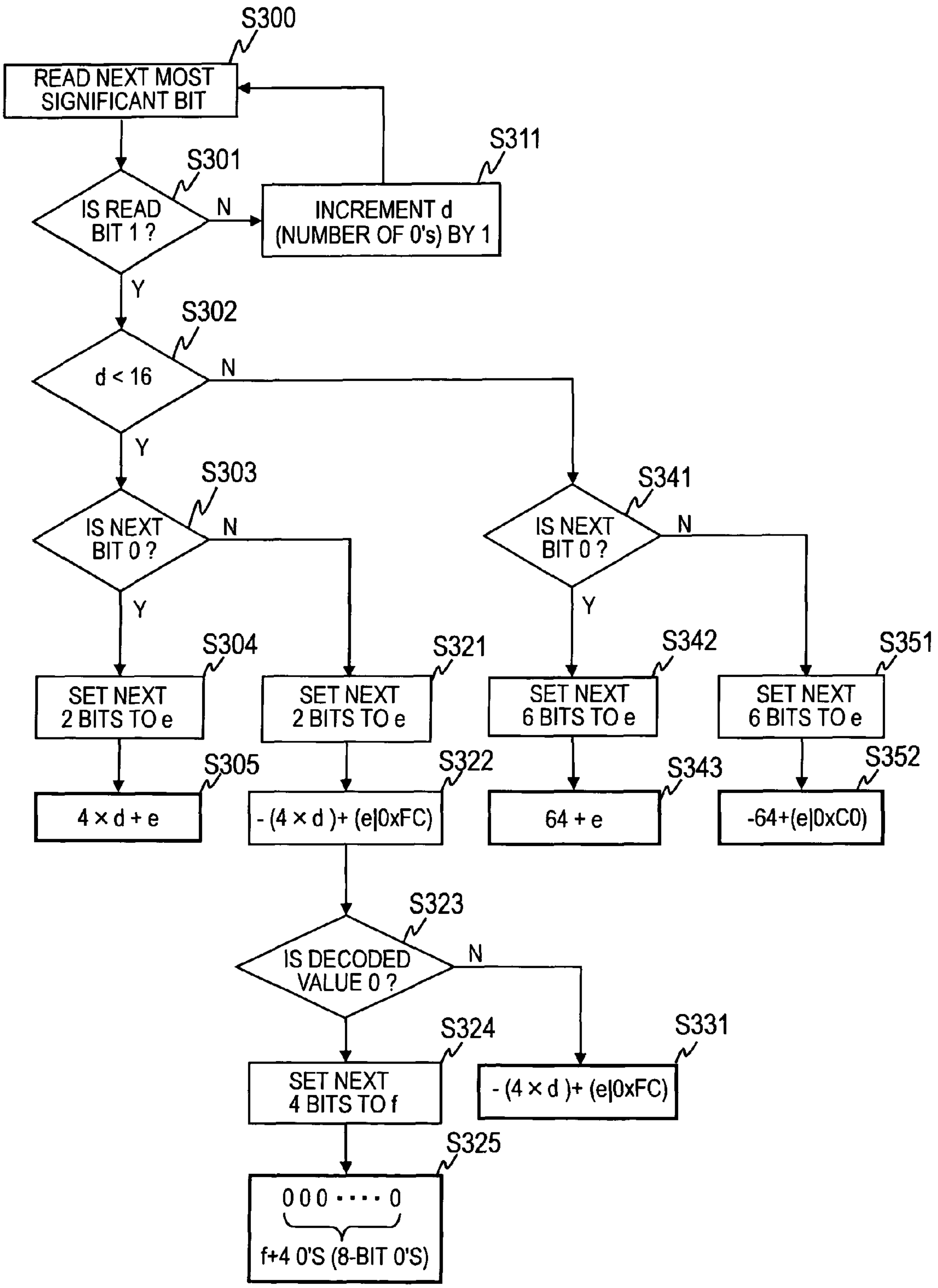
FIG. 23 is a flowchart illustrating an example of a decoding process of compressed sensing data according to the first embodiment.

FIG. 23 is a flowchart for decoding the code shown in FIG. 16. This process is carried out by the decompression program 62 of the gateway 40 executed by the CPU 46.

In the gateway 40, if a data ID 154 read from a received packet data indicates that a payload is compressed sensing data, the CPU 46 carries out the process shown in FIG. 23.

In a step S300, the CPU 46 starts reading values from the MSB of the sensing data to be decoded. In a step S301, if the value of the bit is 1, the CPU 46 proceeds to a step S302, and if the value is 0, the CPU 45 proceeds to a step S311. In the step S311, the CPU 46 adds one to a variable d (initially 0), and returns to the step S300.

In the step S302, if the variable "d"<16, the CPU 46 proceeds to a step S303. Otherwise, the CPU 46 proceeds to a step S341. In other words, the value of the variable "d" is the value of the variable "a" which indicates the position of the delimiter bit (number of bits) shown in FIG. 17 with respect to the MSB. Then, depending on whether the distance of the delimiter bit from the MSB is less than 16 bits, in other words, whether the original sensing data is less than 64, the formats defined by the code table shown in FIG. 16 are switched, and thus the CPU 46 determines which format is used.

In the step S303, if a bit next to the bit which is determined as 1 in the step S301 is 0, the CPU 46 proceeds to a step S 304. Otherwise, the CPU 46 proceeds to a step S321. In other words, the CPU 46 determines whether the sign bit on the LSB side of the delimiter bit indicates positive data or negative data.

In the step S304, which is the case of positive data indicated by the sign bit of 0, the CPU 46 reads the next two bits, and sets a value thereof to a variable "e". In other words, the CPU 46 reads the "b" bits shown in FIG. 17, and the CPU 46, in a step S305, multiplies the value of the variable "d", which is the value of the variable "a", by 4, adds the value of the variable "e" to the product, sets the sum as the original positive sensing data, and completes the process.

On the other hand, if the sensing data is less than 64, and negative, which is indicated by the sign bit of 1, the CPU 46, in the step S321, reads the next two bits ("b" bits), and sets a value thereof to the variable "e". In other words, the CPU 46 reads "b" bits shown in FIG. 17, and the CPU 46, in a step S322, multiplies the value of the variable "d", which is the value of the variable "a", by 4, adds the value of the variable "e" to the product, multiplies the sum by −1, and sets the product as the original negative sensing data.

Then, in a step S323, the CPU 46 determines whether the value of the decoded sensing data is 0. If the value of the sensing data is not 0, the CPU 46 proceeds to a step S331, outputs the value obtained in the step S323 as a result of the decoding, and completes the process.

If the sensing data is negative, and zero, namely "−0" as shown in FIG. 16, the sensing data indicates four or more successive 0's, and the CPU 46 carries out further decoding starting from a step S324.

In the step S324, the CPU 46 reads the four bits on the LSB side, which are "b" bits, and sets the four bits to a variable "f". In a step S325, the CPU 46 generates f+4 successive 0's (eight bits), which is a series of sensing data, outputs the f+4 of 0's as a result of the decoding, and completes the process.

If the CPU 46 determines that the sensing data to be decoded is 64 or more in the step S302, the CPU 46 determines whether the sign bit next to the delimiter bit which is determined as 1 on the LSB side is 0 or not in the step S341. If the sign bit is 0, the sensing data is positive, and the CPU 46 proceeds to a step S342. If the sign bit is 1, the sensing data is negative, and the CPU 46 proceeds to a step S351.

In the step S342, the CPU 46 reads next six bits on the LSB side of the sign bit ("b" bits) and sets the six bits to the variable "e". In a step S343, the CPU 46 adds 64 to the value of the variable "e", outputs the sum as decoded sensing data, and completes the process.

If the sensing data is negative, the CPU 46 reads the next six bits on the LSB side of the sign bit, which are "b" bits, and sets the six bits to the variable "e" in the step S 351. In a step S352, the CPU 46 adds 64 to the value of the variable "e", multiplies the sum by −1, and outputs the product as decoded sensing data, and completes the process.

As a result of the above-mentioned processes, in the gateway 40, the sensing data compressed by encoding is decoded from the data of the RF packet data.

It should be noted that the decoding process shown in FIG. 23 may be carried out on the server 43. In this case, the gateway 40 does not carry out the decoding process, and simply transfers the RF packet data received from the sensor node 1 directly to the server 43.

Figure 24:
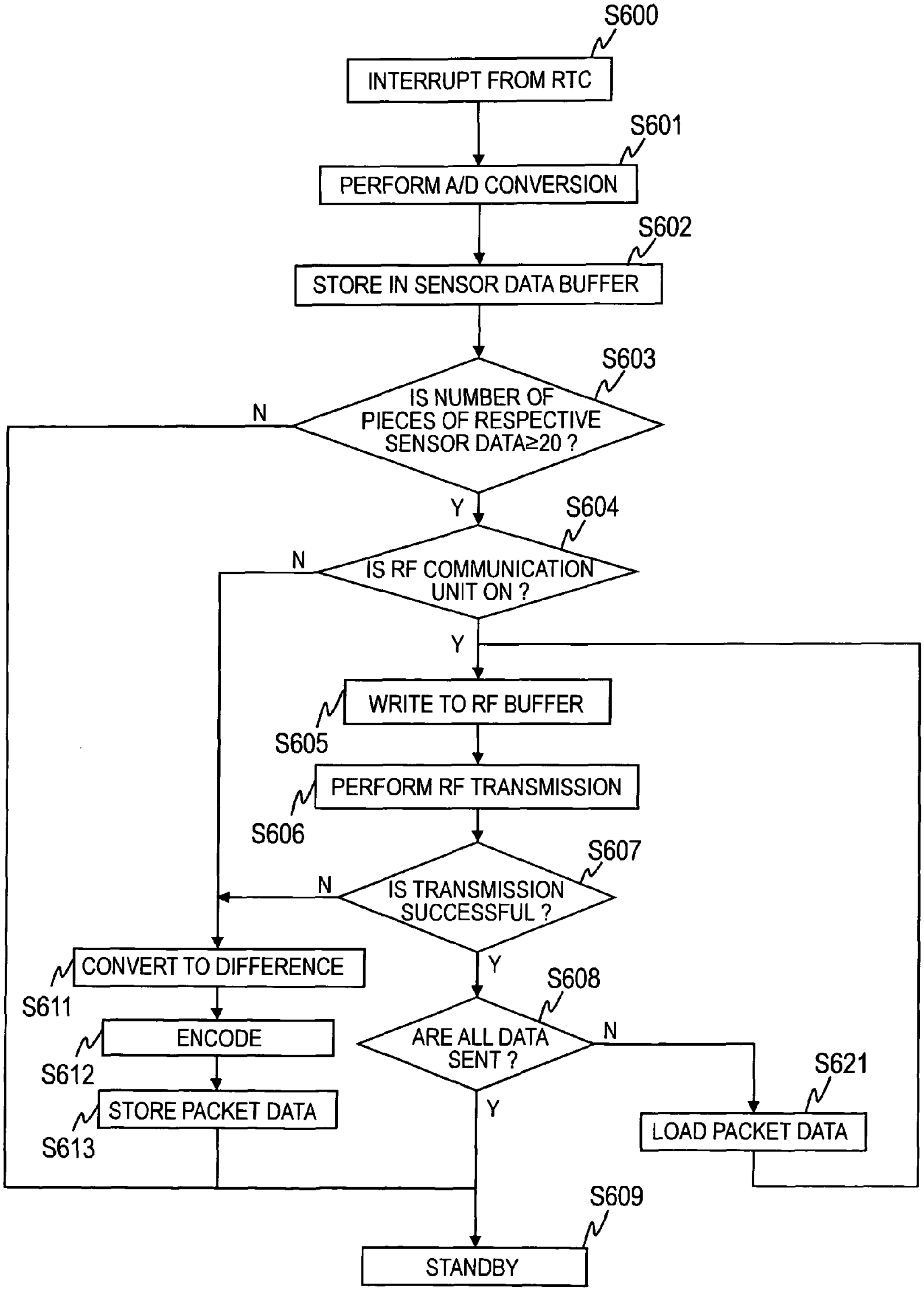
FIG. 24 is a flowchart illustrating an example of a timer interruption process carried out on the sensor node according to the first embodiment.

FIG. 24 is a flowchart illustrating an example of a process carried out on the sensor node 1. This process starts on the occasion when the CPU 28 is started by an interrupt by the RTC 14. The period (sampling period) of the interrupt of the RTC 14 is set to 50 milliseconds, for example, and is set by the CPU 28 to the RTC 13 when the sensor node 1 is started up.

In a step S600, the microcomputer 20 during the standby state is started up according to the sampling period by a signal transmitted from the RTC 14 to the interrupt control unit 29. In a step S601, the CPU 28 turns on the switch 15 to start supplying the acceleration sensor 12 with the electric power, and acquires sensing data from the acceleration sensor 12 by means of the A/D conversion carried out by the A/D converter 23. In a step S602, the CPU 28 stores the sensing data converted into a digital value in the sensor data buffer 53. In a step S603, if the number of the respective sensing data stored in the sensor data buffer 53 is equal to or more than 20, the CPU 28 proceeds to a step S604. Otherwise, the CPU 28 proceeds to a step S609.

In the step S604, the CPU 28 determines whether the RF communication unit 11 is on or off. If the RF communication unit 11 is on, the CPU 28 proceeds to a step S605 in order to wirelessly transmit the sensing data (RF packet data). If the RF communication unit 11 is off, the CPU 28, the CPU 28 proceeds to a step S611 in order to compress the sensing data, and store the compressed sensing data in the RF buffer 52.

In the step S605, the CPU 28 stores the RF packet data in the RF buffer 52, and carries out the RF transmission in a step S606. In a step S607, if the RF transmission in the step S606 is successful, the CPU 28 proceeds to a step S608, and if the RF transmission failed, the CPU 28 proceeds to a step S611. If the RF transmission is successful, the CPU 28 deletes the RF packet data in the RF buffer 52.

In the step S608, the CPU 28 determines whether unsent RF packet data is left in the RF buffer 52 of the RAM 25. If no unsent RF packet data is left, the CPU 28 proceeds to a step S609. If unsent RF packet data is left in the RF buffer 52, the CPU 28 proceeds to a step S621. In the step S621, the CPU 28 loads the RF packet data stored in the memory (RAM 25 or the flash memory 30), and proceeds to the step S605.

In the step 611, which is performed when the CPU 28 determines that the RF communication unit 11 is turned off in the step S604, or that the transmission failed in the step S607, the CPU 28 carries out the conversion into the difference representation shown in FIG. 20 for the sensing data contained in the RF packet data stored in the RF buffer 52. Then in a step S612, the sensing data converted into the difference representation in the RF packet data is compressed by the encoding shown in FIGS. 16 to 19. In a step S613, the CPU 28 stores the encoded RF packet data (sensing data) and other RF packet data in the packet buffer 54 or the flash memory 30.

In the step S609, the CPU 28 completes the entire process, and the microcomputer 20 turns off the switch 15 thereby shutting off the power supply to the acceleration sensor 12, and transitions to the standby mode.

As a result of the above-mentioned process, the sensor node 1 starts up the microcomputer 20 in the standby mode according to the interrupt from the RTC 14 when the predetermine sampling period starts, carries out the acquisition of sensing data from the acceleration sensor 12 and the RF transmission, carries out the conversion into the difference representation and the encoding of the sensing data contained in the RF packet data if RF transmission fails or if the RF transmission unit 11 turned off, thereby compressing the sensing data if the RF transmission fails or if the RF transmission unit 11 is turned off, and stores the compressed sensing data in the packet buffer 54 or the flash memory 30 for the next RF transmission to be carried out.

The microcomputer 20 remains during the standby state until the next sampling period comes, and the electric power for the acceleration sensor 12 is shut off until the next sampling period comes. These two operations prevent the battery from being consumed.

Figure 25:
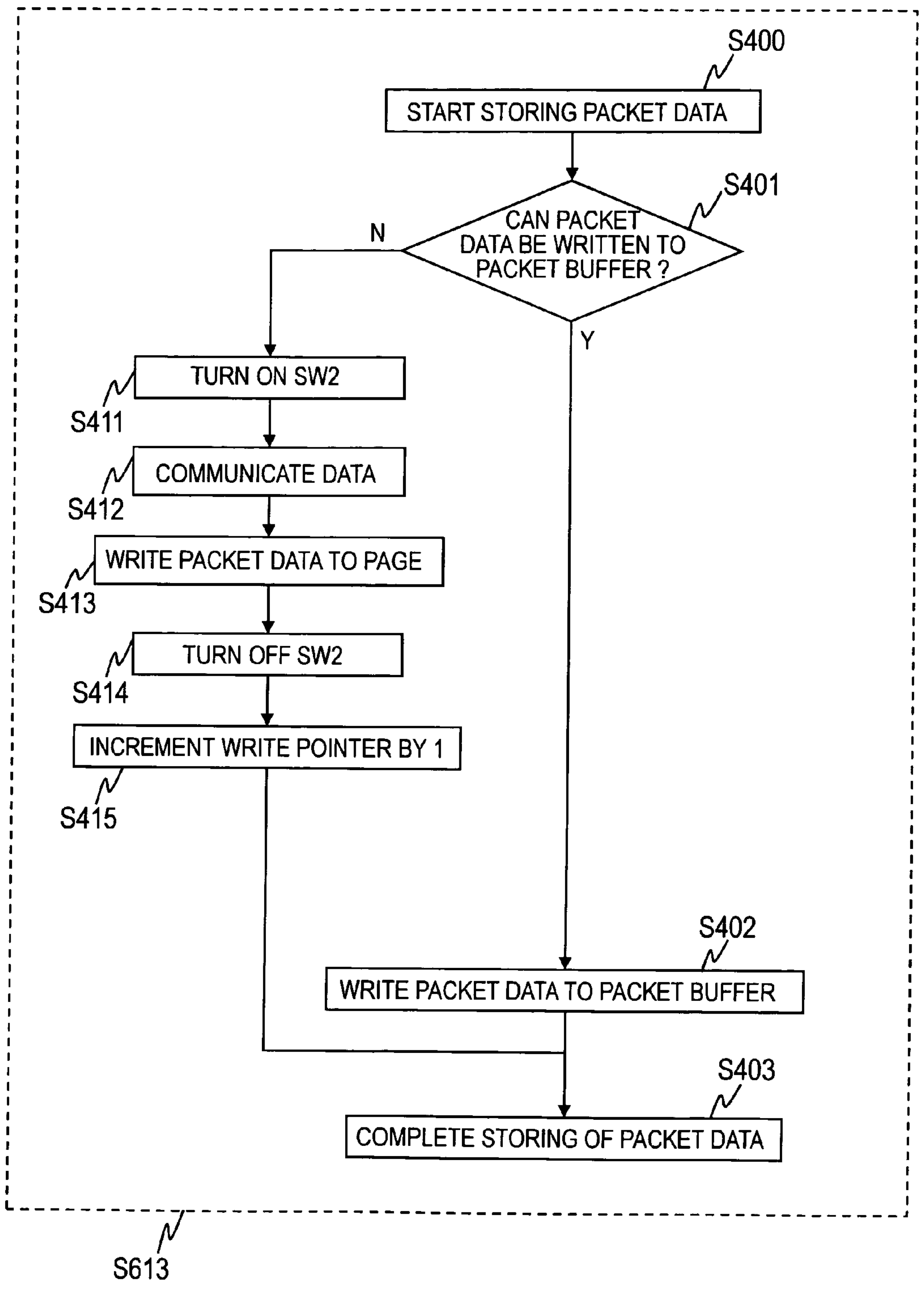
FIG. 25 is a flowchart illustrating in detail a storing process for the RF packet data carried out in a step S613 of FIG. 24 according to the first embodiment.

FIG. 25 is a flowchart illustrating in detail the storing process of the RF packet data carried out in the above-mentioned step S613. The CPU 28 starts writing the RF packet data to the memory from a step S400. In a step S401, if the CPU 28 can write the RF packet data to the packet buffer 54 of the RAM 25, the CPU 28 proceeds to a step S402, and if the CPU 28 cannot write the RF packet data due to the lack of the free capacity of the packet buffer 54, the CPU 28 proceeds to a step S411. In the step S402, the CPU 28 writes the RF packet data to the packet buffer 54. In a step S403, the CPU 28 completes the storing of the packet data, and returns to the process shown in FIG. 24.

On the other hand, if the CPU 28 determines that the CPU 28 cannot write the RF packet data to the packet buffer 54 in the step S401, the CPU 28 turns on the switch 16 by controlling the parallel interface 26, thereby turning on the flash memory 30 in the step S411.

In a step S412, the CPU 28 transfers the packet data in the packet buffer 54 to the read/write buffer 31 of the flash memory 30 via the serial communication interface 27. In a step S413, the CPU 28 writes the packet data to the page 34 of the memory cell 32 pointed by the write pointer 51.

In a step S414, when the CPU 28 completes the writing, the CPU 28 turns off the switch 16 by controlling the parallel interface 26, thereby shutting off the electric power supplied to the flash memory 30. In a step S415, the CPU 28 increments the value of the write pointer 51 by one. If there is no more page address 33 after the increment of the value of the write pointer 51 by one, the CPU 28 sets the value of the write pointer 51 to the top page address 33. Moreover, the CPU 28 deletes the packet data in the packet buffer 54 which has been written. In the step S403, the CPU 28 completes the storing of the packet data, and returns to the process shown in FIG. 24.

With the above-mentioned processes, the CPU 28 starts writing the compressed RF packet data in the packet buffer 54 of the RAM 25 when the CPU 28 cannot carry out the RF communication. As soon as the packet buffer 54 becomes full, the CPU 28 turns on the flash memory 30, and writes the packet data stored in the packet buffer 54 at once to the flash memory 30. Then, when the CPU 28 completes the writing of the packet data, the CPU 28 turns off the power supply to the flash memory 30, thereby preventing the battery 17 from being consumed.

Moreover, for the write to the flash memory 30, it is possible to use the pages 34 thereof while circulating from the top page to the end page according to the write pointer 51, thereby preventing a concentrated rewrite on specific pages 34, resulting in an extended service life of the flash memory 30.

Figure 26:
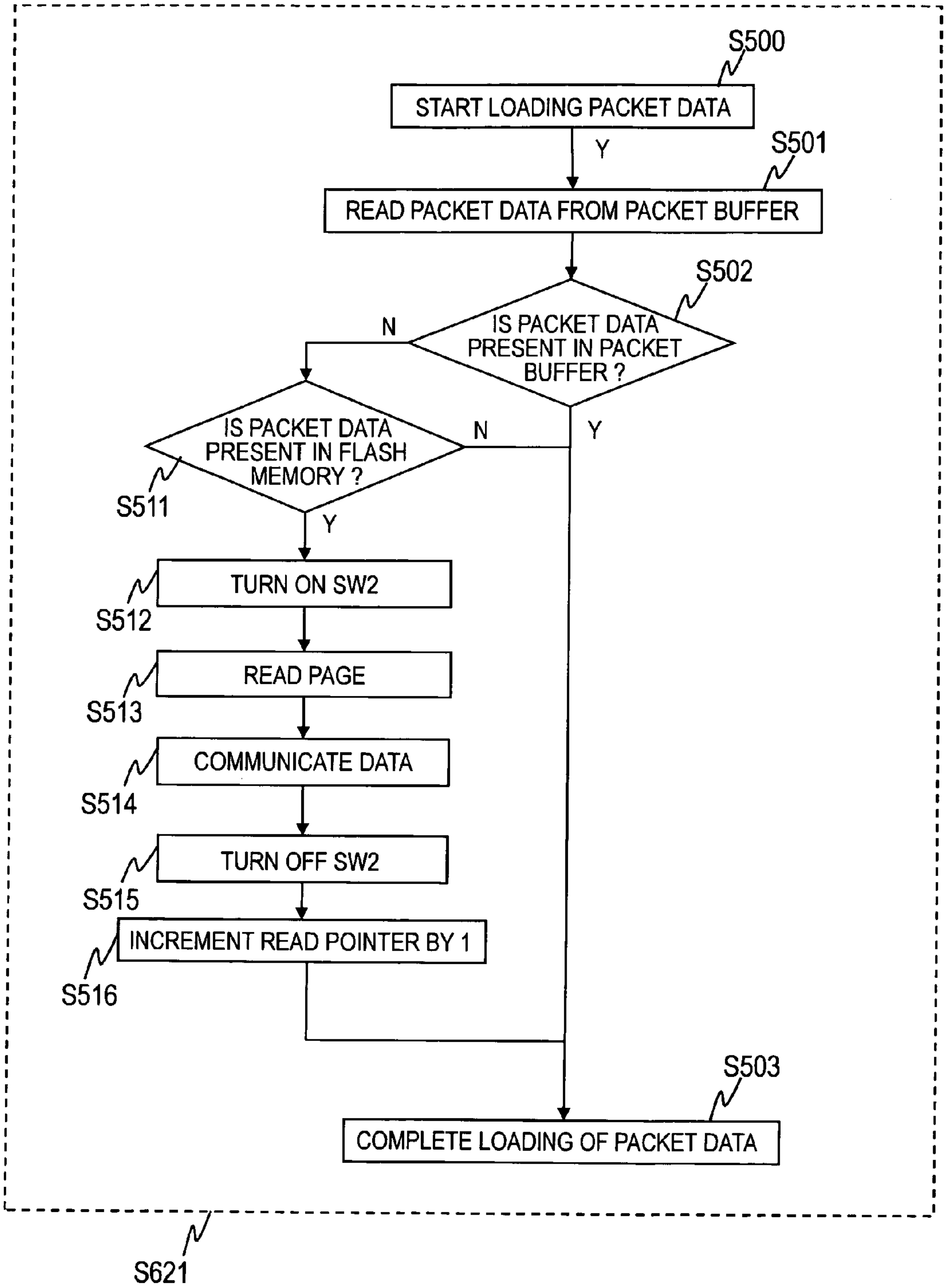
FIG. 26 is a flowchart illustrating in detail a loading process for the RF packet data carried out in a step S621 of FIG. 24 according to the first embodiment.

FIG. 26 is a detailed flowchart of a packet data loading process carried out in the step S621 in FIG. 24.

In a step S500, the CPU 28 starts loading RF packet data. In a step S501, the CPU 28 reads unsent RF packet data from the packet buffer 54, and transfers the read RF packet data to the RF buffer 52. In a step S502, if unsent packet data exists in the packet buffer 54, the CPU 28 proceeds to a step S503, and if no unsent packet data exists in the packet buffer 54, the CPU 28 proceeds to a step S511.

In the step S511, if unsent packet data exists in the flash memory 30, the CPU 28 proceeds to a step S512, and if no unsent packet data exists, the CPU 28 proceeds to the step S503. The existence of unsent RF packet data in the flash memory 30 in the step S511 is determined depending on whether the value of the read pointer 50 and the value of the write pointer 51 coincide with each other or not. If the values of the pointers 50 and 51 coincide with each other, the CPU 28 determines that no unsent RF packet data exists.

In a step S512, the CPU 28 turns on the switch 16 by controlling the parallel interface 26, thereby starting the power supply to the flash memory 30. In a step S513, the CPU 28 reads the RF packet data from a page 34 of the flash memory 30 pointed by the read pointer 50 to the read/write buffer 31. In a step S514, the CPU 28 reads the RF packet data via the serial communication interface 27 to the packet buffer 54.

In a step S515, the CPU 28 turns off the switch 16 by controlling the parallel interface 26, thereby shutting off the power supply to the flash memory 30. In a step S516, the CPU 28 increments the value of the read pointer 50 by one. If the read pointer 50 no longer points to an existing page address 33 as a result of the increment by one, the CPU 28 sets the top page address 33 to the read pointer 50. In the step S503, the CPU 28 completes the loading of the RF packet data.

As the write operation of RF packet data shown in FIG. 25, by supplying the flash memory 30 with the electric power only during the read period, it is possible to prevent the battery 17 from being consumed, thereby decreasing the frequency of the maintenance of the sensor node 1.

Figure 27:
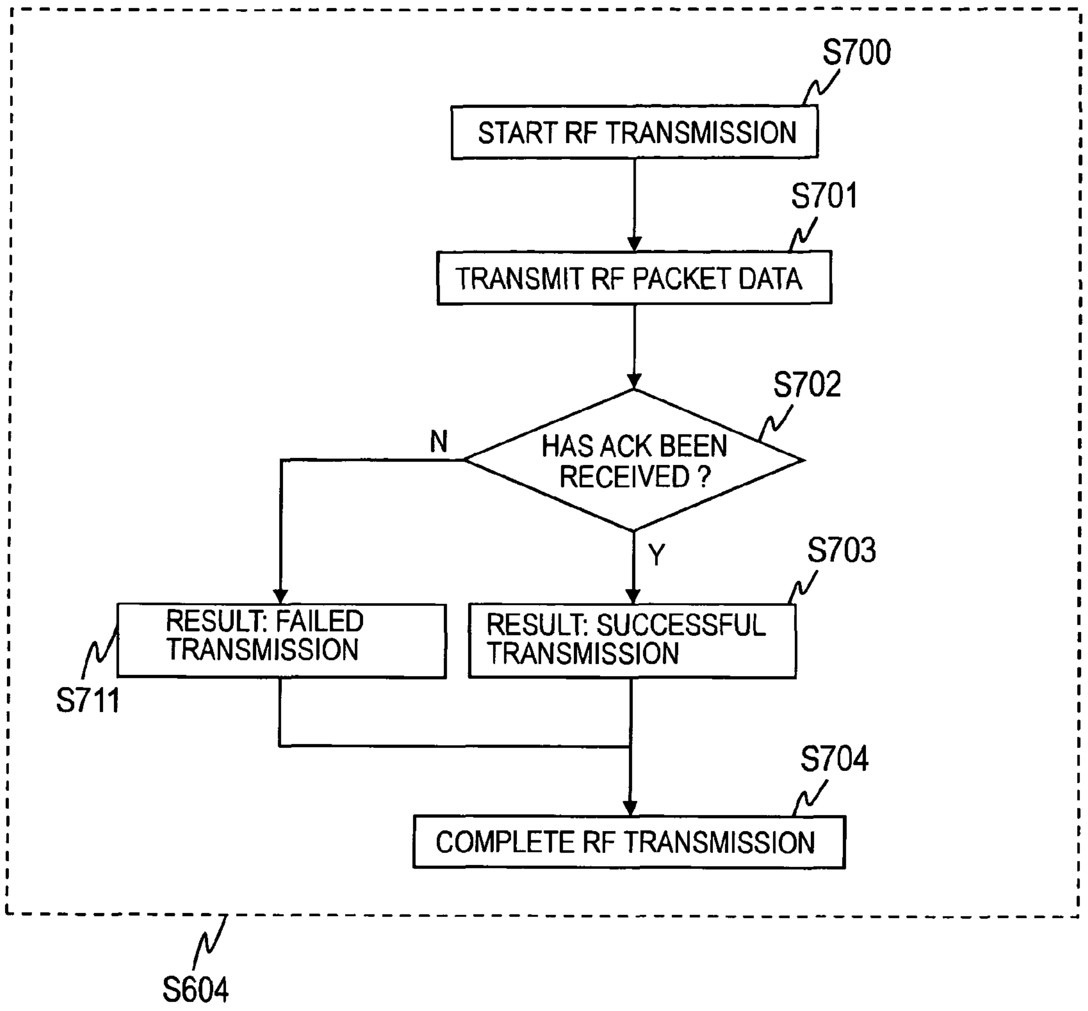
FIG. 27 is a flowchart illustrating in detail an RF transmission process carried out in a step S606 of FIG. 24 according to the first embodiment.

FIG. 27 is a flowchart illustrating in detail the RF transmission process in the step S606 shown in FIG. 24. In a step S701, the CPU 28 transmits data in the RF buffer 52 (RF packet data) from the RF communication unit 11. In a step S702, if the CPU 28 receives an ACK packet in response to the RF transmission in the step S701 from the gateway 40, the CPU proceeds to a step S703, and if the CPU 28 does not receive an ACK packet, the CPU proceeds to a step S711.

In the step S703, the CPU 28 determines that the RF transmission succeeded, and in the step S711, the CPU 28 determines that the RF transmission failed. In a next step S704, the CPU 28 completes the RF transmission process.

According to the above-mentioned process, the CPU 28 determines whether the RF communication succeeded or failed.

In this way, according to the first embodiment, sensing data (RF packet data) acquired in a period during which the RF communication is not available, is compressed by means of the conversion into the difference representation, and the encoding, and then, is stored in the packet buffer 54 of the RAM 25 or the flash memory 30, it is possible to retain a large amount of the sensing data on the sensor node 1 which is limited in the computer resources. As a result, the sensing data such as the acceleration is required to be measured at a relatively short sampling period. However, by compressing the sensing data by means of the conversion into the difference representation and the encoding while the RF communication is not available, it is possible to retain more sensing data with the limited storage capacity of the sensor node 1, and to prevent a lack of the sensing data to be accumulated in the server 43.

Moreover, since sensing data is compressed when the sensing data is to be stored in the packet buffer 54 or the flash memory 30, and sensing data is not compressed when the sensing data can be directly transmitted, it is possible to reduce the electric power consumed by the arithmetic process carried out by the CPU 28, thereby preventing the battery 17 from being consumed.

Moreover, since the flash memory 30 which stores sensing data which cannot be transmitted is supplied with the electric power only when the read or write operation is carried out thereon, it is possible to prevent the battery 17 from being consumed. Therefore, it is possible to increase the maintenance interval of the battery 17 mounted on the sensor node 1, thereby making the sensor node 1 more convenient to use.

Moreover, since the write operation to the flash memory 30 serving as a non-volatile memory circulates from the top page to the end page successively switching the pages 34, it is possible to prevent specific pages 34 from being frequently rewritten, thereby extending the service life of the flash memory 30.

Moreover, in the method of encoding according to this invention, as the a plurality of pieces of sensing data becomes closer to zero, the compression ratio increases, and a plurality of pieces of sensing data of successive 0's are combined into one piece of data, thereby further increasing the compression ratio. As a result, when 0 frequently appears throughout the day as in the data of an acceleration of a living organism, it is possible to increase the overall data compression ratio, thereby enabling sensing data to be held in the storage unit of the sensor node 1 limited in capacity while the RF communication is not available.

Further, as the storage unit for holding the sensing data (RF packet data), the RAM 25 configured of the volatile storage unit, and the flash memory 30 configured of the rewritable non-volatile storage unit are provided, and the RF buffer 52 of the RAM 25, which is fast in access and low in power consumption, is used for the transmission of the sensing data. When the RF transmission unit 11 cannot carry out the transmission, sensing data is compressed and stored in the packet buffer 54 of the RAM 25, thereby preventing the flash memory 30, which consumes a large electric power, from being used.

Then, since the a plurality of pieces of RF packet data are written to the flash memory 30 at once when the packet buffer 54 becomes full (when the number of RF packet data reaches the predetermined number), the period of the operation of the flash memory 30 which consumes a large electric power during the rewrite, can be reduced as much as possible. As a result, the consumption of the battery 17 can be prevented as much as possible.

Moreover, since the button switches 18 and 19 used for turning on and off only the RF communication unit 11 is provided, it is possible to continue the measurement of biological information even in an environment where the RF communication is restricted, while only the RF communication unit 11 is turned off without turning off the entire sensor node 1.

Second Embodiment

Figure 28:
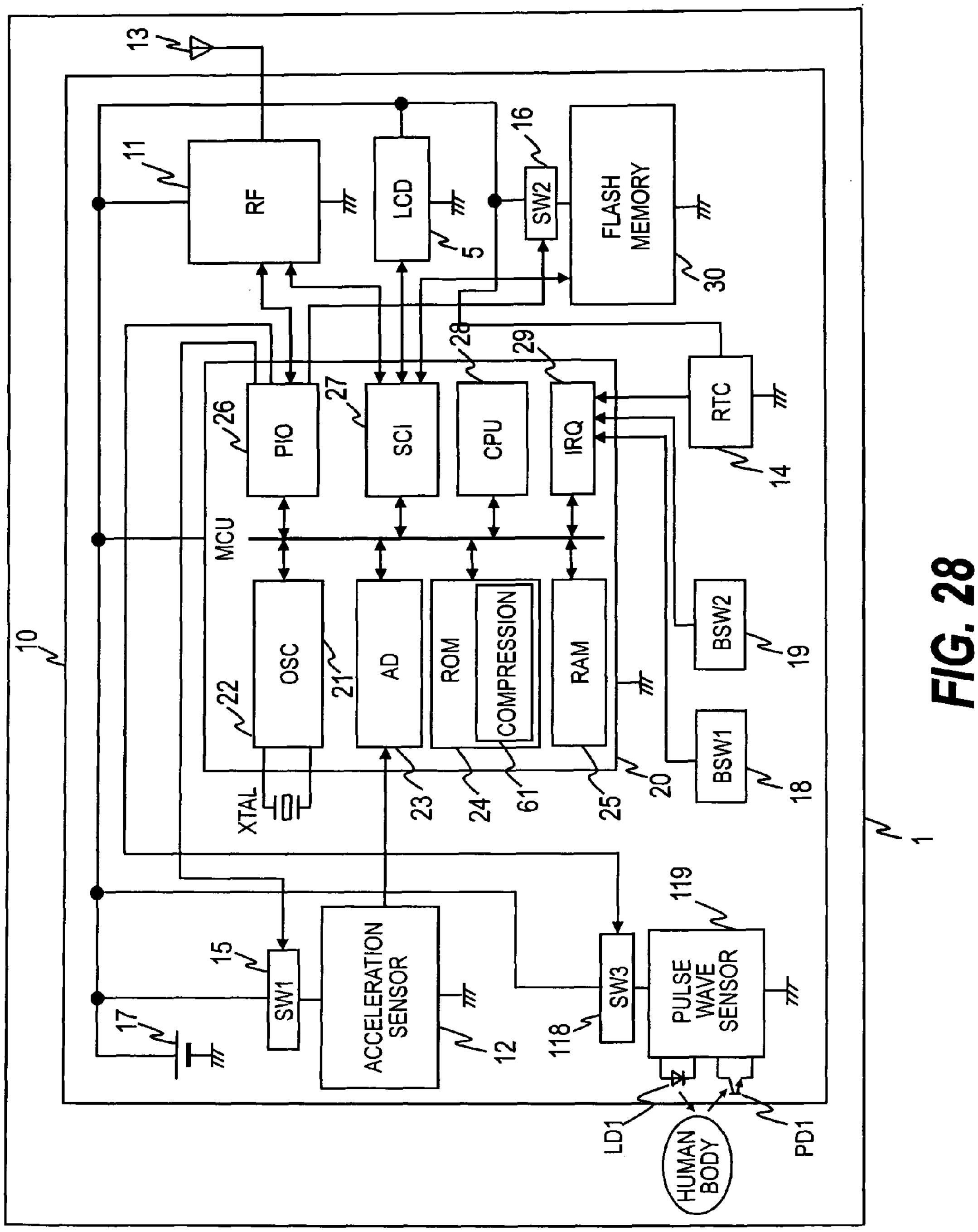
FIG. 28 is a block diagram of a sensor network system according to a second embodiment.

FIG. 28 illustrates a block diagram of an electronic circuit mounted on the circuit board 10 of the sensor node 1 according to a second embodiment of the present invention, and a pulse wave sensor 19 shown in a lower left section of FIG. 28 is added to the configuration of the first embodiment of the present invention. The second embodiment includes the pulse wave sensor 119 in addition to the acceleration sensor 12 according to the first embodiment, and the other configuration thereof is the same as the configuration of the first embodiment of the present invention.

This pulse wave sensor 119 employs an infrared light emitting diode as a light emitting element LD1, and a phototransistor as a light receiving element PD1. It should be noted that a photodiode may be used as the light receiving element PD1 in place of the phototransistor. On a rear surface of the case 3, the light emitting element LD1 and the light receiving element PD1 are exposed, and can oppose the skin of the arm.

This pulse wave sensor 119 radiates the infrared light emitted from the light emitting element LD1 on blood vessels under the skin, and detects an intensity change of scattered light from the blood vessels caused by fluctuations in blood flows on the light receiving element PD1, thereby estimating the pulse and the pulse wave according to the frequency of a change in an intensity thereof.

The pulse wave sensor 119 is connected to the A/D converter 23 as the acceleration sensor 6, and an analog output thereof is converted into a digital value. Moreover, a power supply used to drive the pulse wave sensor 119 is the battery 17 to which the pulse wave sensor 119 is connected via a switch 118. The switch 118 is controlled by the parallel interface 26 as the switch 15 according the first embodiment of the present invention, thereby turning on/off an electric power supplied to the pulse wave sensor 119. The timing of the pulse wave sensor 119 is controlled as the timing of the acceleration sensor 12 according to the first embodiment of the present invention, and the power supply thereof is turned on when the measurement period starts, and is turned off during the inactive period.

For the measurement of the pulse by the pulse sensor 119, it is desirable the living organism (user) be in the resting state. When the wearer is moving, waveforms of the pulse are disturbed, and thus, the normal pulse cannot be correctly detected. This is because the pulse wave sensor 119 is not in close contact with the arm, and thus is exposed to external light interference at a time interval much shorter than the pulse period, resulting in the disturbed waveforms of the pulse. Thus, in order to detect reliable pulse wave, it is necessary to carry out the sensing when the user is resting. According to the second embodiment of the present invention, the accelerations along three axes and the pulse wave are measured on the same timing as the first embodiment of the present invention, and a plurality of pieces of RF packet data are transmitted to the gateway 40 at once. In order to use these RF packet data, pulse wave acquired when it is recognized that the sensing data for the acceleration is indicating the resting state may be employed.

Figure 29A:
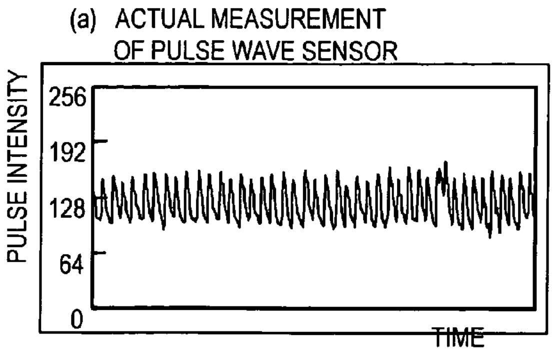
FIG. 29A is a graph illustrating a relationship between pulse intensity and time acquired by the sensor node when the pulse of a person was sensed according to the second embodiment.
Figure 29B:
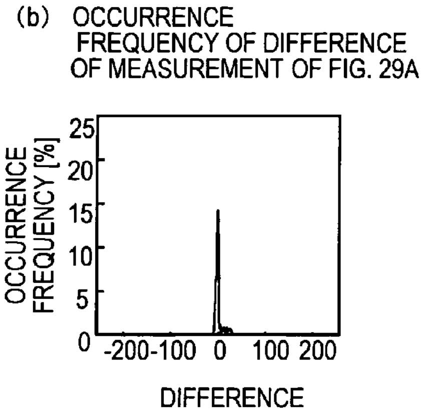
FIG. 29B is a graph illustrating a relationship between the difference representation of the pulse intensity and an occurrence frequency thereof acquired by the sensor node when the pulse of a person was sensed according to the second embodiment.

FIG. 29A illustrates an actual measurement by the pulse waveform sensor 119. This measurement was obtained when a wearer is in a resting state, and thus illustrates a precise pulse waveform. FIG. 29B illustrates an occurrence frequency in the difference representation converted from the measurement. This illustrates that the occurrence frequency of the sensing data is unevenly distributed as the acceleration waveforms (as described in FIGS. 13 to 15). However, the highest occurrence frequency of the difference is not zero, which is different from the acceleration waveforms. This is because, though a rate of change in the pulse waveform in the resting state is centered on a certain value, the pulse wave is always changing, and thus, the rate of change is not zero. However, by changing the arrangement of the encoding defined in the code table shown in FIG. 16 according to the change rate of the pulse wave, it is possible to provide a high compression ratio.

Figure 30:
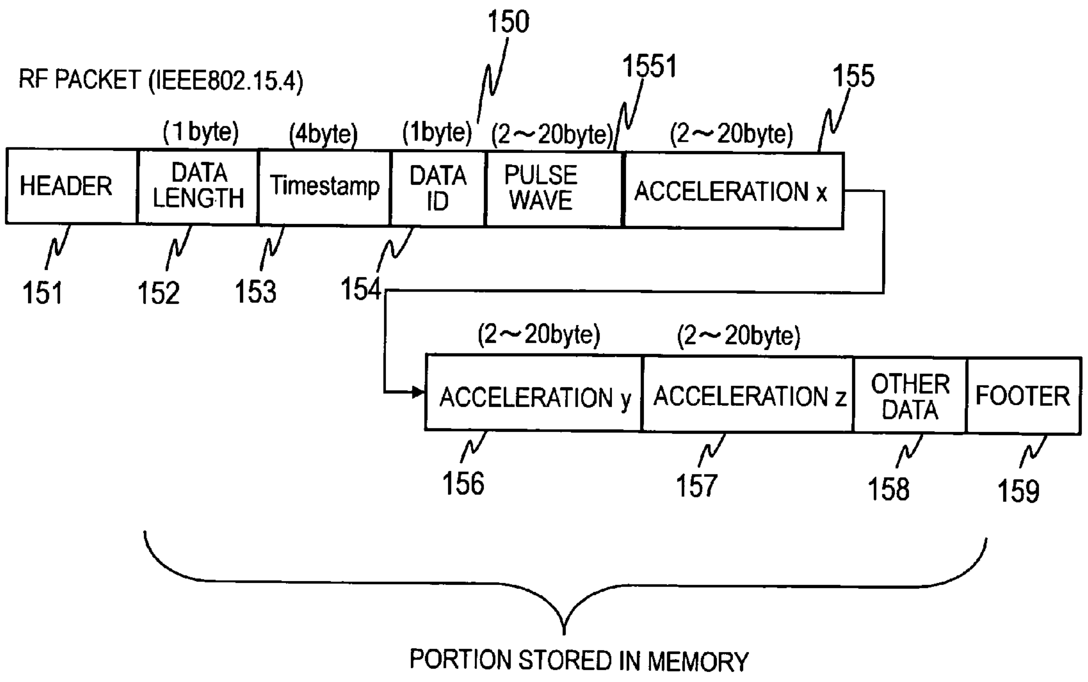
FIG. 30 is a block diagram illustrating a configuration of an RF packet transmitted by the sensor node according to the second embodiment.

FIG. 30 illustrates a format 150 of an RF packet generated as is the case with the first embodiment of the present invention shown in FIG. 21. A plurality of (20, for example) pieces of pulse wave sensing data are acquired from the pulse waveform sensor 119, and are stored in a compressed or uncompressed form in a section 1551.

Figure 31:
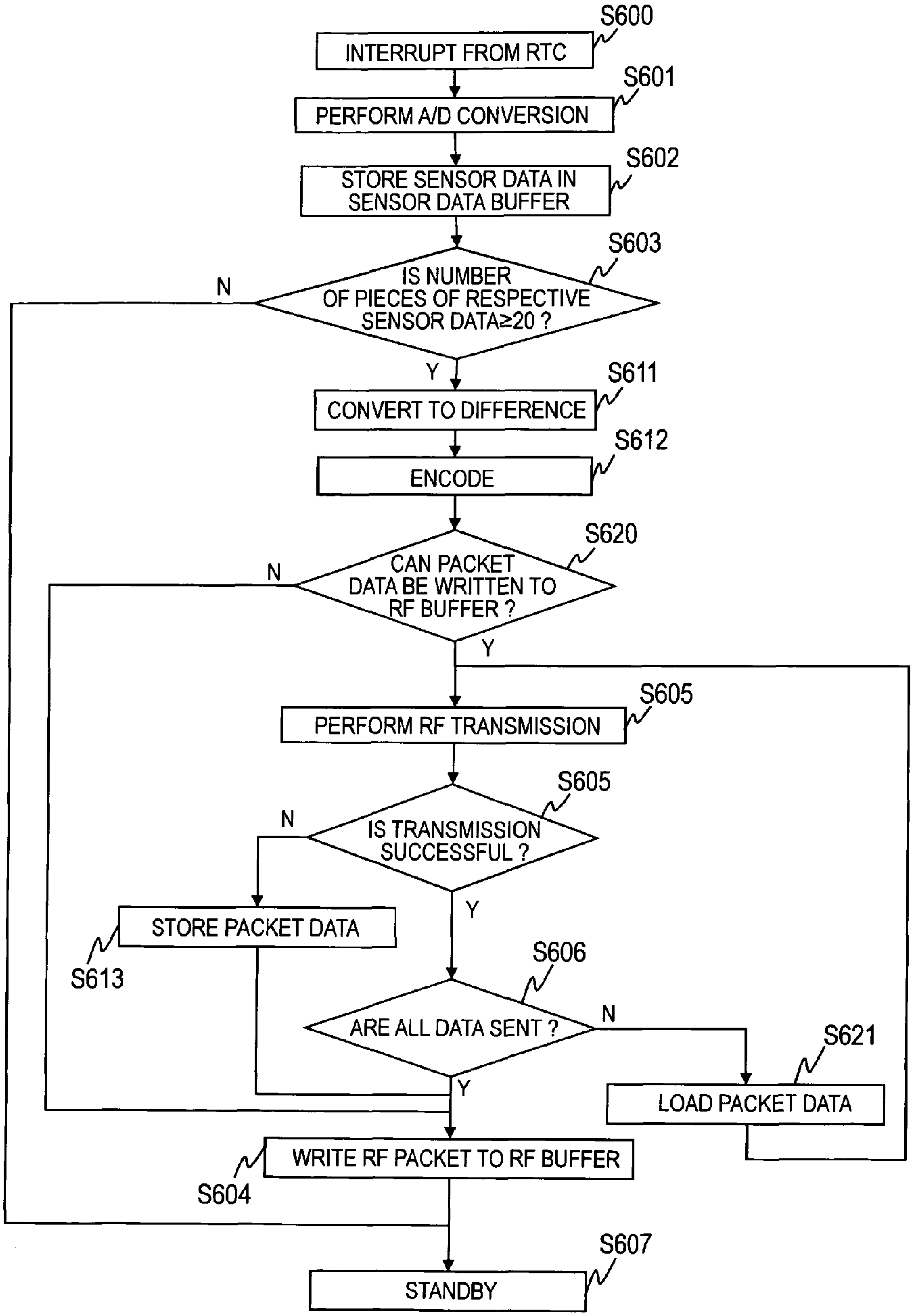
FIG. 31 is a flowchart illustrating an example of a timer interruption process carried out on the sensor node according to the second embodiment.

It is possible to reduce the quantity of the data to be wirelessly transmitted by compressing RF packet data to be immediately transmitted as well as RF packet data to be retained, which is different from the first embodiment. FIG. 31 illustrates a flowchart for an operation on the sensor node 1 in this case.

In steps S600 to S602, as in the first embodiment of the present invention shown in FIG. 24, the CPU 28 stores sensing data in the sensor data buffer 53.

In a step S603, if the number of respective sensing data≧20, the CPU 28, in a step S604, immediately converts the sensor data into the difference representation as in the first embodiment of the present invention, and, in a step S605, encodes the converted sensing data as in the first embodiment. In a step S620, the CPU 28 determines whether RF packet data carrying the encoded sensing data can be written in a free space in the RF buffer 52. If the RF packet data cannot be written in a free space, the CPU 28 wirelessly transmits the RF packet data in a step S605, and if the RF packet data can be written in a free space, the CPU 28 proceeds to a step S604. In the step S604, the CPU writes the RF packet data containing the encoded sensing data in the free space of the RF buffer 52.

As described above, by applying the conversion into the difference representation and the encoding to, in addition to the sensing data retained in the sensor node 1, the sensing data contained in the RF packet data to be transmitted from the sensor node 1, it is possible to reduce the data quantity for the RF transmission, thereby reducing the period required for the communication. As a result, it is possible to reduce the electric power consumed by the RF communication unit 11, thereby preventing the battery 17 from being consumed.

It should be noted that according to the above-mentioned embodiments, the encoding is carried out according to the flowcharts shown in FIGS. 18 and 19, but the encoding may be carried out according to the table shown in FIG. 16.

It should be noted that according to the above-mentioned respective embodiments, but the acceleration and the pulse wave are measured as the biological information, these embodiments may be applied to a sensor node 1 for detecting the heartbeat rate or the like.

<Note>

A method carried out by a sensor node provided with a sensor for transmitting biological information measured by the sensor, including the steps of:

acquiring data from the sensor for measuring the biological information;

storing the data in a volatile storage unit of the sensor node;

transmitting the data stored in the volatile storage unit via a radio frequency transmission unit of the sensor node;

determining whether the transmission has been completed or not;

compressing the data stored in the volatile storage unit if the transmission has not been completed;

supplying a non-volatile storage unit provided on the sensor node with an electric power;

writing the compressed data in the non-volatile storage unit; and shutting off the power supply to the non-volatile storage unit.

As described above, this invention can be applied to a sensor node and a sensor network system employing the sensor node for measuring information at a predetermined sampling period.

While the present invention has been described in detail and pictorially in the accompanying drawings, the present invention is not limited to such detail but covers various obvious modifications and equivalent arrangements, which fall within the purview of the appended claims.

What is claimed is:

1. A sensor node comprising:

a sensor for measuring biological information;

a control unit for acquiring data by driving the sensor, the data including an acceleration value;

a wireless communication unit for transmitting the data acquired by the control unit;

a battery for supplying the control unit, the wireless communication unit, and the sensor with electric power;

a volatile storage unit for storing the data;

a compression unit for compressing the data stored in the volatile storage unit when the wireless communication unit cannot carry out the transmission if and only if the acceleration value included in the data is less than or equal to a predetermined value, the compression unit comprising a difference representation conversion unit for converting the data into differences between the data and an encoding unit for converting a first difference that is smaller than a second difference into a shorter length code than that of the second difference; and a non-volatile storage unit for storing the compressed data.

2. The sensor node according to claim 1, wherein the control unit comprises a switch for starting, upon start of an access to the non-volatile storage unit, supplying the non-volatile storage unit with the electric power, and stopping, upon end of the access to the non-volatile storage unit, supplying the non-volatile storage unit with the electric power.

3. The sensor node according to claim 1, wherein:

the non-volatile storage unit comprises a plurality of pages each of which is a predetermined unit of write; and the control unit, upon write of data to the non-volatile storage unit, successively switches the plurality of pages while circulating from a top page toward an end page.

4. The sensor node according to claim 1, wherein the compression unit comprises an encoding unit for converting the data into a predetermined variable length code.

5. The sensor node according to claim 1, wherein the control unit comprises a wireless communication inactivation unit for switching the wireless communication unit to one of an inactive state and an active state.

6. The sensor node according to claim 1, wherein:

the volatile storage unit comprises a buffer for storing the data; and the control unit stores one of the acquired data and the data read from the non-volatile storage unit in the buffer, and transfers the data in the buffer to the wireless communication unit to transmit the data.

7. A sensor network system comprising:

a sensor node for transmitting data measured by a sensor for measuring biological information, the data including an acceleration value; and a relaying apparatus for receiving the data and transferring the received data to a server computer, wherein:

the sensor node comprises:

a control unit for acquiring data by driving the sensor;

a wireless communication unit for transmitting the data acquired by the control unit;

a battery for supplying the control unit, the wireless communication unit, and the sensor with electric power;

a volatile storage unit for storing the data;

a compression unit for compressing the data stored in the volatile storage unit when the wireless communication unit cannot carry out the transmission if and only if the acceleration value included in the data is less than or equal to a predetermined value, the compression unit comprising a difference representation conversion unit for converting the data into differences between the data and an encoding unit for converting a first difference that is smaller than a second difference into a shorter length code than that of the second difference; and a non-volatile storage unit for storing the compressed data; and the relaying apparatus comprises:

a wireless communication unit for communicating with the sensor node;

a decoding unit for decoding the data received from the sensor node; and a network communication unit for transmitting the decoded data to the server computer.

8. The sensor network system according to claim 7, wherein the control unit comprises a switch for starting, upon start of an access to the non-volatile storage unit, supplying the non-volatile storage unit with the electric power, and stopping, upon end of the access to the non-volatile storage unit, supplying the non-volatile storage unit with the electric power.

9. The sensor network system according to claim 7, wherein:

the non-volatile storage unit comprises a plurality of pages each of which is a predetermined unit of write; and the control unit, upon write of data to the non-volatile storage unit, successively switches the plurality of pages while circulating from a top page toward an end page.

10. The sensor network system according to claim 7, wherein the compression unit comprises an encoding unit for converting the data into a predetermined variable length code.

11. The sensor network system according to claim 7, wherein the control unit comprises a wireless communication inactivation unit for switching the wireless communication unit to one of an inactive state and an active state.

12. The sensor network system according to claim 7, wherein:

the volatile storage unit comprises a buffer for storing the data; and the control unit stores one of the acquired data and the data read from the non-volatile storage unit in the buffer, and transfers the data in the buffer to the wireless communication unit to transmit the data.

13. A sensor network system comprising:

a sensor node for transmitting data measured by a sensor for measuring biological information, the data including an acceleration value; and a relaying apparatus for receiving the data and transferring the received data to a server computer, wherein:

the sensor node comprises:

a control unit for acquiring data by driving the sensor;

a wireless communication unit for transmitting the data acquired by the control unit;

a battery for supplying the control unit, the wireless communication unit, and the sensor with electric power;

a volatile storage unit for storing the data;

a compression unit for compressing the data stored in the volatile storage unit when the wireless communication unit cannot carry out the transmission if and only if the acceleration value included in the data is less than or equal to a predetermined value, the compression unit comprising a difference representation conversion unit for converting the data into differences between the data and an encoding unit for converting a first difference that is smaller than a second difference into a shorter length code than that of the second difference; and a non-volatile storage unit for storing the compressed data;

the relaying apparatus comprises:

a wireless communication unit for communicating with the sensor node; and a network communication unit for transmitting the data received from the sensor node to the server computer; and the server computer comprises:

a communication unit for communicating with the relaying apparatus;

a decoding unit for decoding the data received from the relaying apparatus; and a data storage unit for storing the decoded data.

14. The sensor network system according to claim 13, wherein the control unit comprises a switch for starting, upon start of an access to the non-volatile storage unit, supplying the non-volatile storage unit with the electric power, and stopping, upon end of the access to the non-volatile storage unit, supplying the non-volatile storage unit with the electric power.

15. The sensor network system according to claim 13, wherein:

the non-volatile storage unit comprises a plurality of pages each of which is a predetermined unit of write; and the control unit, upon write of data to the non-volatile storage unit, successively switches the plurality of pages while circulating from a top page toward an end page.

* * * * *

UNITED STATES PATENT AND TRADEMARK OFFICE

CERTIFICATE OF CORRECTION

PATENT NO. : 8,330,596 B2
APPLICATION NO. : 12/155457
DATED : December 11, 2012
INVENTOR(S) : Tanaka et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 699 days.

Signed and Sealed this
Eighteenth Day of November, 2014

Michelle K. Lee
*Deputy Director of the United States Patent and Trademark Office*